(12) United States Patent
Campbell et al.

(10) Patent No.: US 7,988,290 B2
(45) Date of Patent: Aug. 2, 2011

(54) SYSTEMS AND METHODS FOR MEASURING THE SHAPE AND LOCATION OF AN OBJECT

(75) Inventors: Charles E. Campbell, Berkeley, CA (US); Stephen W. Farrer, Albuquerque, NM (US); Daniel R. Neal, Tijeras, NM (US); William S. Powers, Albuquerque, NM (US); Thomas D. Raymond, Edgewood, NM (US); James Copland, Albuquerque, NM (US)

(73) Assignee: AMO Wavefront Sciences LLC., Santa Ana, CA (US)

( * ) Notice: Subject to any disclaimer, the term of this patent is extended or adjusted under 35 U.S.C. 154(b) by 241 days.

(21) Appl. No.: 12/347,909

(22) Filed: Dec. 31, 2008

(65) Prior Publication Data

US 2009/0161090 A1 Jun. 25, 2009

Related U.S. Application Data

(63) Continuation-in-part of application No. 11/769,054, filed on Jun. 27, 2007.

(60) Provisional application No. 61/019,807, filed on Jan. 8, 2008.

(51) Int. Cl.
*A61B 3/10* (2006.01)
(52) U.S. Cl. ...................................................... 351/212
(58) Field of Classification Search .................. 351/205, 351/206, 210, 211, 212, 221, 240–247; 606/3, 606/4, 5, 10, 13
See application file for complete search history.

(56) References Cited

U.S. PATENT DOCUMENTS

| | | | |
|---|---|---|---|
| 4,159,867 A | 7/1979 | Achatz et al. | |
| 4,312,574 A | 1/1982 | Wilms | |
| 4,420,228 A | 12/1983 | Humphrey | |
| 4,440,477 A | 4/1984 | Schachar | |
| 4,530,579 A | 7/1985 | Hyde | |
| 4,558,270 A | 12/1985 | Liautaud et al. | |
| 4,569,576 A | 2/1986 | Karpov et al. | |

(Continued)

FOREIGN PATENT DOCUMENTS

DE 19538567 4/1997
(Continued)

OTHER PUBLICATIONS

"Object surface for applying a modified Hartmann test to measure corneal topography," Applied Optics, vol. 40, No. 31 (Nov. 1, 2001) ("Mejía-Barbosa").

(Continued)

*Primary Examiner* — William C Choi
*Assistant Examiner* — Tuyen Tra

(57) ABSTRACT

A system for determining the shape of an object and/or a distance of the object from the system includes a first plurality of light source, a second plurality of light sources, and a detector or detector array. The first plurality of light sources are disposed about a central axis and are separated from the central axis by radial distances defining an aperture in the first plurality of light sources. The system also includes an optical system adapted to provide light from the second plurality of light sources through the aperture to the object. The system may further include a computer configured to determine the shape of the object and/or the distance of the object from the system using light from the first and second plurality of light sources that is reflected from the object and received by the detector.

25 Claims, 21 Drawing Sheets

U.S. PATENT DOCUMENTS

| | | | |
|---|---|---|---|
| 4,662,730 A | 5/1987 | Outwater et al. | |
| 4,666,269 A | 5/1987 | Nakamura et al. | |
| 4,761,071 A | 8/1988 | Baron | |
| 4,902,123 A | 2/1990 | Yoder, Jr. | |
| 4,917,458 A | 4/1990 | Matsumura | |
| 4,993,826 A | 2/1991 | Yoder, Jr. | |
| 4,998,819 A | 3/1991 | Labinger et al. | |
| 5,054,907 A | 10/1991 | Sklar et al. | |
| 5,062,702 A | 11/1991 | Bille | |
| 5,106,183 A | 4/1992 | Yoder, Jr. | |
| 5,110,200 A | 5/1992 | Snook | |
| 5,283,598 A | 2/1994 | McMillan et al. | |
| 5,349,398 A | 9/1994 | Koester | |
| 5,392,079 A | 2/1995 | Fedorov et al. | |
| 5,418,582 A | 5/1995 | Van Saarloos | |
| 5,493,109 A | 2/1996 | Wei et al. | |
| 5,500,697 A | 3/1996 | Fujieda | |
| 5,585,873 A | 12/1996 | Shalon et al. | |
| 5,640,962 A | 6/1997 | Jean et al. | |
| 5,684,562 A | 11/1997 | Fujieda | |
| 5,777,719 A | 7/1998 | Williams et al. | |
| 5,793,468 A | 8/1998 | Shalon et al. | |
| 5,847,804 A | 12/1998 | Sarver et al. | |
| 5,864,383 A | 1/1999 | Turner et al. | |
| 5,867,250 A | 2/1999 | Baron | |
| 5,873,832 A | 2/1999 | Maloney et al. | |
| 5,886,767 A | 3/1999 | Snook | |
| 5,909,270 A | 6/1999 | Moser et al. | |
| 5,920,373 A | 7/1999 | Bille | |
| 5,929,970 A | 7/1999 | Mihashi | |
| 5,953,100 A | 9/1999 | Sarver et al. | |
| 5,993,000 A | 11/1999 | Kobayashi et al. | |
| 6,004,314 A | 12/1999 | Wei et al. | |
| 6,007,204 A | 12/1999 | Fahrenkrug et al. | |
| 6,042,233 A | 3/2000 | Mihashi et al. | |
| 6,048,065 A | 4/2000 | Davis et al. | |
| 6,050,687 A | 4/2000 | Bille et al. | |
| 6,059,773 A | 5/2000 | Maloney et al. | |
| 6,070,981 A | 6/2000 | Mihashi et al. | |
| 6,079,831 A | 6/2000 | Sarver et al. | |
| 6,086,204 A | 7/2000 | Magnante | |
| 6,116,738 A | 9/2000 | Rorabaugh | |
| 6,120,150 A | 9/2000 | Sarver et al. | |
| 6,129,722 A | 10/2000 | Ruiz | |
| 6,152,565 A | 11/2000 | Liu et al. | |
| 6,234,631 B1 | 5/2001 | Sarver et al. | |
| 6,234,978 B1 | 5/2001 | Mihashi et al. | |
| 6,257,723 B1 | 7/2001 | Sarver et al. | |
| 6,271,914 B1 | 8/2001 | Frey et al. | |
| 6,271,915 B1 | 8/2001 | Frey et al. | |
| 6,299,309 B1 | 10/2001 | Ruiz | |
| 6,305,802 B1 | 10/2001 | Roffman et al. | |
| 6,379,008 B1 | 4/2002 | Chateau et al. | |
| 6,382,795 B1 | 5/2002 | Lai | |
| 6,394,605 B1 | 5/2002 | Campin et al. | |
| 6,409,344 B1* | 6/2002 | Hayashi | 351/208 |
| 6,428,168 B2 | 8/2002 | Sarver et al. | |
| 6,447,119 B1 | 9/2002 | Stewart et al. | |
| 6,454,761 B1 | 9/2002 | Freedman | |
| 6,460,997 B1 | 10/2002 | Frey et al. | |
| 6,467,907 B1 | 10/2002 | Fujieda et al. | |
| 6,497,483 B2 | 12/2002 | Frey et al. | |
| 6,511,179 B1 | 1/2003 | Davis et al. | |
| 6,511,180 B2 | 1/2003 | Guirao et al. | |
| 6,525,883 B2 | 2/2003 | Hirohara et al. | |
| 6,540,692 B2 | 4/2003 | Mihashi et al. | |
| 6,547,393 B2 | 4/2003 | Ruiz | |
| 6,550,917 B1 | 4/2003 | Neal et al. | |
| 6,565,209 B2 | 5/2003 | Campin | |
| 6,569,154 B2 | 5/2003 | Campin et al. | |
| 6,572,230 B2 | 6/2003 | Levine | |
| 6,575,573 B2 | 6/2003 | Lai et al. | |
| 6,592,574 B1 | 7/2003 | Shimmick et al. | |
| 6,598,973 B2 | 7/2003 | Campin | |
| 6,598,975 B2 | 7/2003 | Liang et al. | |
| 6,601,956 B1 | 8/2003 | Jean et al. | |
| 6,607,273 B2 | 8/2003 | Sarver et al. | |
| 6,609,794 B2 | 8/2003 | Levine | |
| 6,610,048 B1 | 8/2003 | Holladay et al. | |
| 6,616,275 B1 | 9/2003 | Dick et al. | |
| 6,629,761 B1 | 10/2003 | Hirohara et al. | |
| 6,634,752 B2 | 10/2003 | Curatu | |
| 6,637,884 B2 | 10/2003 | Martino | |
| 6,666,857 B2 | 12/2003 | Smith | |
| 6,685,320 B2 | 2/2004 | Hirohara et al. | |
| 6,692,126 B1 | 2/2004 | Xie et al. | |
| 6,695,450 B2 | 2/2004 | Hirohara et al. | |
| 6,705,729 B2 | 3/2004 | Piers et al. | |
| 6,739,721 B2 | 5/2004 | Altmann | |
| 6,755,528 B2 | 6/2004 | Isogai | |
| 6,755,819 B1 | 6/2004 | Waelti | |
| 6,808,266 B2 | 10/2004 | Youssefi | |
| 6,814,729 B2 | 11/2004 | Youssefi et al. | |
| 6,827,444 B2 | 12/2004 | Williams et al. | |
| 6,848,790 B1 | 2/2005 | Dick et al. | |
| 6,905,209 B2 | 6/2005 | Mihashi et al. | |
| 6,913,358 B2 | 7/2005 | Manuel Martins Borges De Almeida et al. | |
| 6,926,408 B2 | 8/2005 | Sarver | |
| 6,939,342 B2 | 9/2005 | Markman | |
| RE38,839 E | 10/2005 | Magnante | |
| 6,988,801 B2 | 1/2006 | Yoon | |
| 7,029,119 B2 | 4/2006 | Youssefi et al. | |
| 7,036,934 B1 | 5/2006 | Youssefi et al. | |
| 7,044,603 B2 | 5/2006 | Yoon | |
| 7,044,944 B2 | 5/2006 | Campin et al. | |
| 7,133,137 B2 | 11/2006 | Shimmick | |
| 7,146,983 B1 | 12/2006 | Hohla et al. | |
| 7,216,980 B2 | 5/2007 | Mihashi et al. | |
| 7,222,962 B2 | 5/2007 | Hirohara et al. | |
| 7,226,443 B1 | 6/2007 | Campin et al. | |
| 7,237,898 B1 | 7/2007 | Hohla et al. | |
| 7,249,851 B2 | 7/2007 | Hirohara et al. | |
| RE39,882 E | 10/2007 | Mihashi et al. | |
| 7,303,281 B2 | 12/2007 | Wakil et al. | |
| 7,309,126 B2 | 12/2007 | Mihashi et al. | |
| 7,635,186 B2 | 12/2009 | Kobayashi et al. | |
| 2002/0026181 A1 | 2/2002 | O'Donnell, Jr. | |
| 2003/0169403 A1 | 9/2003 | Curatu | |
| 2004/0021826 A1 | 2/2004 | Sarver et al. | |
| 2004/0066489 A1 | 4/2004 | Benedikt et al. | |
| 2005/0018136 A1 | 1/2005 | Hayashi | |
| 2005/0124983 A1* | 6/2005 | Frey et al. | 606/5 |
| 2006/0084956 A1 | 4/2006 | Sumiya | |
| 2006/0152677 A1 | 7/2006 | Youssefi et al. | |
| 2006/0209256 A1 | 9/2006 | Beyerlein et al. | |
| 2007/0013918 A1 | 1/2007 | Hauger et al. | |
| 2007/0032782 A1 | 2/2007 | Youssefi et al. | |
| 2007/0078447 A1 | 4/2007 | Weinacht et al. | |

FOREIGN PATENT DOCUMENTS

| | | |
|---|---|---|
| FR | 2828396 | 2/2003 |
| JP | 11164816 A2 | 6/1999 |
| MX | 1010791 A | 6/2003 |
| WO | WO03063695 A1 | 8/2003 |
| WO | WO03077740 A1 | 9/2003 |

OTHER PUBLICATIONS

Liang J. et al., "Objective measurement of wave aberrations of the human eye with the use of a Hartmann-Shack wave-front sensor," J Opt Soc Am A Opt Image Sci Vis, 1994, 11 (7), 1949-1957.

Massig Juergen H. et al., "Videokeratoscope for accurate and detailed measurement of the cornea surface," Optical Society of Americal, 2005, vol. 44 (12).

Mejia-Barbosa, "Correlation-Based Method for Comparing and Reconstructing Nearly Identical Two-Dimensional Structures," Appl Opt, pp. 235-239 , 2001, vol. 40 (1).

Rubinstein J., et al., "Reconstruction of Optical Surfaces from Ray Data", Optical Review, pp. 281-283, 2001, vol. 8 (4).

Salmon T., et al, "Corneal Contribution to the Wavefront Aberration of the Eye," Indiana University Graduate School, 1999.

Sicam et al, "Corneal Surface Reconstruction Algorithm that uses Zernike Polynomial Representation," J Opt Soc Am A Opt Image Sci Vis, pp. 1300-1306, 2004, vol. 21 (7), Optical Society of America.

Wang M., "Corneal Topography in the Wavefront ERA: A Guide to Clinical Application," Topographic Technologies, Chap. 4.

* cited by examiner

SYSTEMS AND METHODS FOR MEASURING THE SHAPE AND LOCATION OF AN OBJECT

RELATED APPLICATION

This application is a continuation-in-part of, and claims prior to, U.S. patent application Ser. No. 11/769,054, filed on Jun. 27, 2008, and further claims priority to U.S. provisional application No. 61/019,807, filed on Jan. 8, 2008, the entire contents of each of which applications are hereby incorporated by reference in their entirety for all purposes as if fully set forth herein.

BACKGROUND AND SUMMARY

1. Field

This invention pertains to the field of optical diagnostics, and in particular to methods and systems for measuring the shape and location of an object such as a cornea of an eye.

2. Description

Optical diagnostic systems provide information of an object without the necessity of physical contact. For example, surface topography or optical characteristics of an eye or ophthalmic lens may be obtained using any of a variety of optical techniques, including optical topography, optical coherence tomography, interferometry, aberrometry, and the like. In some instances, accurate measurements depend on knowing or moving the test object to a precise location.

In the field of ophthalmics, ocular aberrations of the eye typically produce unwanted results (bad eyesight) and therefore need to be characterized so as to be adequately treatable. Wavefront measurement systems and methods have been developed for measuring ocular aberrations of an eye. One class of such systems typically provide a probe beam to illuminate the eye and measure the wavefront of light refracted from the eye to measure the total aberrations of the eye.

Since typically 60-70% of ocular aberrations result from imperfections in the cornea, such wavefront measurements can be more valuable if the corneal topography of the eye is known. Topographical measurements of a cornea are typically performed by a corneal topographer. A variety of corneal topographers are known in the art, examples of which are disclosed in U.S. Pat. Nos. 5,062,702 and 6,634,752, which are herein incorporated by reference for all purposes as if fully set forth herein. It would be useful to provide a combined system for measuring total ocular aberrations and the corneal topography of an eye.

One type of corneal topographer employs a "Placido disk" system. A Placido disk system consists of a series of concentric illuminated rings that are reflected off the cornea of an eye and viewed with a detector array, such as a charge-coupled device or video camera. Other "Placido-type" light sources or systems use other shapes besides rings, for example, a plurality of point sources or relatively small spot sources may be configured in a predetermined pattern.

As used herein, the term "Placido-type light source" or "Placido-type source" means one or a plurality of individual light sources disposed such that light from each of the individual light sources reflects off of a reference or test object, passes through an imaging system, and is received by a detector, wherein light from the Placido-type light source passes only once through the imaging system, or the individual optical elements thereof, and is used to determine geometric and/or optical information of at least a portion of a surface of the reference or test object. The individual light sources may be active sources generating light energy, apertures through which light energy is transmitted, or lighter or more reflective portions of a mask or pattern configured to reflect light. As used herein, the terms "Placido disk" or "Placido disk system" means a system of Placido-type light sources configured as a plurality of rings or annular shapes.

Because of its great simplicity, the Placido disk system has been widely used for measuring corneal topography. A key part of this system is the object surface with rings as well as the spatial distribution and the width of these rings on the surface. The location and width of the rings are computed in such a way that the image of the rings reflected off a reference sphere is a uniform distribution of rings, i.e., rings equally spaced and all with the same width. The radius of curvature of the reference sphere is made equal to the mean radius of the cornea (about 7.8 mm). Then the image of the rings reflected off an aberrated cornea will be distorted rings, and from this distortion it is possible to obtain the shape of the cornea.

Many variations on the Placido disk approach for corneal topography measurements have been developed over the years, examples of which are disclosed in U.S. Pat. Nos. 4,993,826 and 6,601,956, and by Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"), all three references being incorporated herein by reference for all purposes as if fully set forth herein.

One problem in many Placido disk corneal topographers is that the central region of the corneal surface cannot be detected during the measurement because of the need to provide an opening or aperture in the Placido disk for passing the light reflected from the cornea to the detector array. This is especially disadvantageous because the central optical zone of the cornea in particular determines the refractive power of the eye and typically forms the pass-through point of the visual axis. The so-called Stiles-Crawford effect leads to the consequence that the central corneal zone—which is free from any light patterns during the projection of patterns from a Placido disk—plays a special role with respect to the peripheral corneal regions of the eye's projection system. As the opening or aperture is increased in size, this problem is exacerbated.

Another problem with Placido disk corneal topographers is that the data is obtained from analysis of a series of projected rings. That is, a radial position of the detected ring is compared to a reference position and the comparison is used to determine the corneal shape. However, this only provides radial deviations. While these are azimuthally resolved, they do not provide an adequate measure of the "skew" rays, i.e., those rays which would be deflected in an azimuthal direction. This is an inherent limitation for a system using Placido rings. This limitation is especially significant considering that astigmatism, one of the major classes of ocular aberrations, is known to generate significant skew rays.

Yet another problem in Placido-type systems in general, as well as types of optical measurement system (e.g, wavefront aberrometers) is alignment error (i.e., "vertex error") between the corneal surface vertex and the design corneal vertex plane. More specifically, the instrument expects the cornea to be located at a particular location long the optical axis of the system with respect to the Placido disk light sources in order to make accurate calculations of the corneal topography. If an actual cornea being measured is "too close" or "too far" from the instrument, then there is a vertex error that will produce inaccurate corneal topography results, unless this vertex error can be determined and factored into the corneal topography calculations.

Therefore, it would be desirable to provide optical measurement systems that can address one or more of these problems. It would also be desirable to provide a method of measuring aberrations and a corneal topography of an eye. It would further be desirable to provide a corneal topographer that allows the topography of the entire cornea to be characterized. It would still further be desirable to provide a method of determining vertex errors between a corneal topographer and a cornea being measured. It would even further be desirable to provide a corneal topographer that produces a uniform grid of spots on the detector array when an idealized structure (e.g., a "reference cornea") is measured.

In one aspect of the invention, a system measures a corneal topography of an eye. The system includes a group of first light sources arranged around a central axis, the group being separated from the axis by a radial distance defining an aperture in the group; a plurality of second light sources; a detector array; and an optical system adapted to provide light from the second light sources through the aperture to a cornea of an eye, and to provide images of the first light sources and images of the second light sources from the cornea, through the aperture, to the detector array. The optical system includes an optical element having a focal length, f. The second light sources are disposed to be in an optical path approximately one focal length, f, away from the optical element.

In another aspect of the invention, a method of measuring aberrations and a corneal topography of an eye comprises: illuminating a cornea of an eye with light from a group of first light sources arranged around a central axis, the group being separated from the axis by a radial distance defining an aperture in the group; illuminating the cornea with light from a plurality of second light sources, the light passing through the aperture, the second light sources located at an optical infinity relative to the cornea; providing a probe beam through the aperture to a retina of the eye; providing images of the first light sources and images of the second light sources from the cornea through the aperture to a detector array; providing light from the probe beam scattered by the retina through the aperture to a wavefront sensor; determining the cornea topography from an output of the detector array; and determining aberrations of the eye from an output of the wavefront sensor.

In yet another aspect of the invention, a method of measuring a corneal topography of an eye comprises: illuminating a cornea of an eye with a group of first light sources arranged around a central axis, the group being separated from the axis by a radial distance defining an aperture in the group; projecting collimated light beams from a plurality of second light sources, through the aperture, to the cornea; providing images of the first light sources and images of the second light sources from the cornea through the opening in the principal surface to a detector array; and determining the cornea topography from an output of the detector array.

In still another aspect of the invention, a method is provided for determining a vertex alignment error for a corneal topographer comprising central light sources to sample a central region of the corneal surface, and a Placido-type light source array to sample an outer region of the corneal surface outside the central region. The method comprises: measuring, using the central light sources, a curvature in an outer portion of the central region of the corneal surface, adjacent the outer region of the corneal surface; measuring reflection locations from the cornea of an innermost set of light sources of the Placido-type light source array; using the measured curvature of the outer portion of the central region of the corneal surface and the measured reflection locations from the cornea of the innermost set of light sources of the Placido-type light source array to calculate a vertex alignment error for each of the innermost set of light sources of the Placido-type light source; and determining the vertex alignment error for the corneal topographer from the calculated vertex alignment error for each of the innermost set of light sources of the Placido-type light source.

In a further aspect of the invention, a system for measuring a topography of a reflective surface, comprises: an optical element disposed about an optical axis and comprising an object side, the optical element defining an object space located on the object side a finite distance from the optical element and an image space conjugate the object space; at least one first light sources disposed an optically finite distance from the object space and at least one second light source disposed at an optical infinity with respect to the object space; the optical element configured to provide an image within the image space when a reflective surface is disposed within the object space.

In still a further aspect of the invention, a system for measuring a topography of a reflective surface, comprises: an optical element having a focal length and disposed about an optical axis, the optical element comprising an object side and an image side, the optical element defining an object space located on the object side a finite distance from the optical element and an image space located on the image side that is conjugate the object space; at least one first light source disposed an optically finite distance from the object space, and at least one second light source disposed on the image side, the second light source located along an optical path approximately one focal length away from the optical element; the optical element configured to provide an image within the image space when a reflective surface is disposed within the object space.

In yet another aspect of the invention, a system for determining the shape of an object under examination and/or a distance of the object from the system includes a first light source, a second light source, and a detector or detector array. When a surface of a object is illuminated by light from the first and second light sources, (1) the first light source produces a signal at the detector array that depends on a shape of the surface of the object and on a distance of the object from the system, and (2) the second light source produces a signal at the detector array that depends on a shape of the surface of the object and that does not depend on a distance of the object from the system. In certain embodiments, the first light source, second light source, and the detector array are disposed for calculating a distance of the object from the system. Additionally or alternatively, the first light source, second light source, and the detector array are disposed for calculating a shape of the surface of the object. In certain embodiments, the first light source comprise plurality of individual light sources that are disposed about a central axis and are separated from the central axis by radial distances defining an aperture in the first plurality of light sources. The system may also include an optical system adapted to provide light from the second plurality of light sources through the aperture to the object. The system may further include a computer configured to determine the shape of the object and/or the distance of the object from the system using light from the first and second light sources that is reflected from the object and received by the detector.

In another aspect of the invention, a system for measuring a corneal topography of an eye comprises a plurality of light sources disposed about a central axis, a detector array, and an optical system. The light sources are separated from the central axis by radial distances defining an aperture in the plurality. The optical system includes an optical element disposed such that, when the test object is disposed to reflect light from the light sources, light from the plurality of light sources reflects off the test object, passes a time through the optical element, and is received by the detector array to form a plurality of images. Each image of the plurality of images corresponds to one light source of the plurality of light sources, the plurality of images including a first image, a second image, and a third image. The images form a uniform grid pattern when the test object is a sphere having a predetermined radius of curvature. The plurality of light sources are disposed such that the first image, the second image, and the third image each have a different amount of defocus than the other images.

DETAILED DESCRIPTION

As discussed above, it would be desirable to provide systems overcome some of the problems associated with optical measurement systems such as vertex error. Such systems would be particularly beneficial in the areas of metrology and ophthalmic measurement. One example discussed in greater detail herein is a combined system for measuring aberrations and a corneal topography of an eye.

Figure 1A:
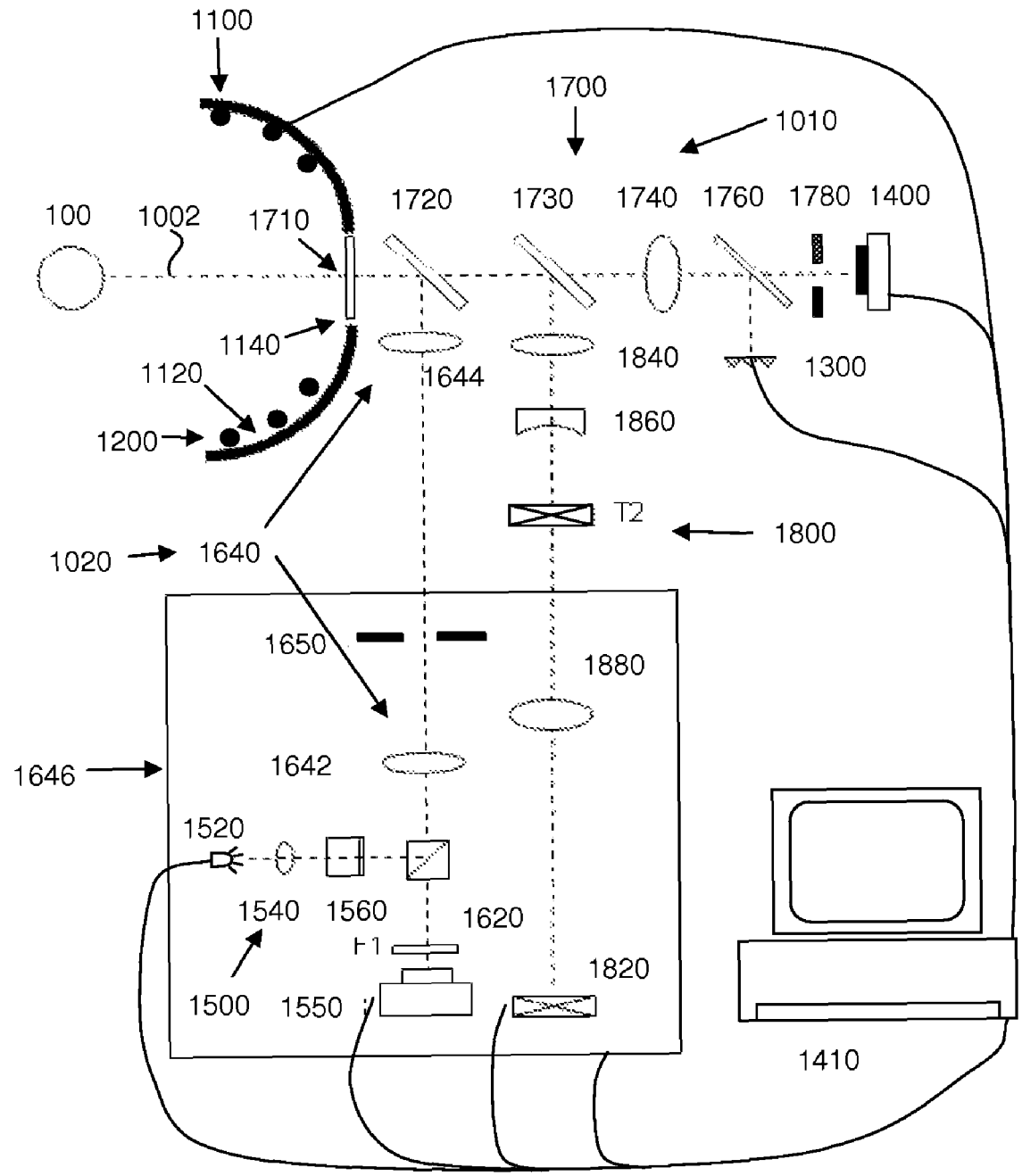
FIG. 1A shows one embodiment of a system for measuring aberrations and corneal topography of an eye.

FIG. 1A shows one embodiment of a system 1000 for measuring aberrations and corneal topography of an eye 100. System 1000 comprises a topographer 1010, an aberrometer or wavefront analyzer 1020, and a processor 1410. The topographer 1010 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); and a detector, photodetector, or detector array 1400.

As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element the refracts, reflects, and/or diffracts light and has either positive or negative optical power.

The wavefront analyzer 1020 of the system 1000 comprises a third light source 1500 providing a probe beam; a wavefront sensor 1550; and an optical system 1700 disposed along a central axis 1002 passing through the opening or aperture 1140 of the structure 1100. Optical system 1700 comprises a quarter wave plate 1710, a first beamsplitter 1720, a second beamsplitter 1730, an optical element (e.g., a lens) 1740, a third beamsplitter 1760, and a structure including an aperture 1780. Beneficially, third light source 1500 includes a lamp 1520, a collimating lens 1540, and light source polarizing beamsplitter 1560. The lamp 1520 may be an SLD or a fiber-coupled source that optionally includes an optical coherence tomographer (OCT). Wavefront analyzer 1020 further comprises a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550 so as to preclude data ambiguity. It will be appreciated by those of skill in the art that the lenses 1642, 1644, or any of the other lenses discussed herein, may be replaced or supplemented by another type of converging or diverging optical element, such as a diffractive optical element. Beneficially, system 1000 further comprises a fixation target system 1800, comprising light source 1820 and lenses 1840, 1860, and 1880.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by a photodetector or electromagnetic image sensor (e.g., a charge-coupled device or CCD) or that is useful in measuring the optical or physical characteristics of an object under examination.

In one embodiment, structure 1100 has the shape of an elongated oval or "zeppelin" with openings or apertures at either end thereof. An example of such a structure is disclosed in Meji'a-Barbosa, cited above, as particularly illustrated in FIG. 4 therein. Such a structure may have an advantage in terms of maintaining the focus of the images of the light spots reflected from the cornea onto detector array 1400.

Figure 4:
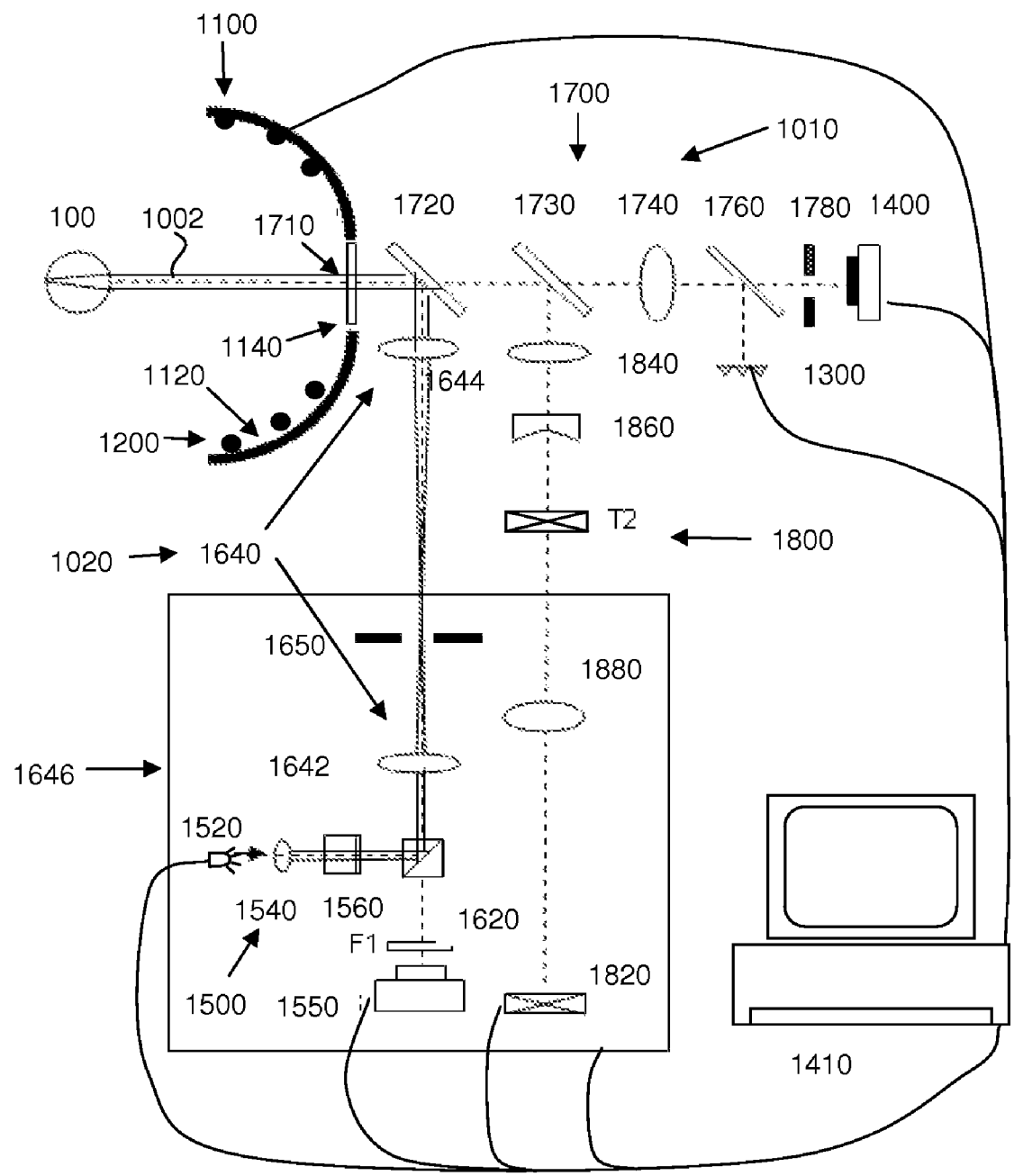
FIG. 4 illustrates rays for a probe beam in the system of FIG. 1A.

However, such a structure has ergonomic disadvantages and may be more difficult to construct than other structures. As can be seen in FIG. 4 of Meji'a-Barbosa, the structure almost appears to be "pointed" in the direction toward the eye, and therefore possibly could cause injury to a patient when aligning the system to a patient's eye.

Accordingly, in some embodiments, principal surface 1120 of structure 1100 is concave when viewed from the cornea of eye 100, as illustrated in FIG. 1A.

In one embodiment where principal surface 1120 is concave, principal surface 1120 has the shape of a conical frustum. Alternatively, principal surface 1120 may have a shape of hemisphere or some other portion of a sphere, with an opening or aperture therein. Also alternatively, principal surface 1120 may have the shape of a modified sphere or conical frustum, with a side portion removed. Beneficially, such an arrangement may improve the ergonomics of system 1000 by more easily allowing structure 1100 to be more closely located to a subject's eye 100 without being obstructed by the subject's nose. Of course, a variety of other configurations and shapes for principal surface 1120 are possible.

In the embodiment of FIG. 1A, the plurality of first light sources 1200 are provided on the principal surface 1120 of structure 1100 so as to illuminate the cornea of eye 100. In one embodiment, light sources 1200 may comprise individual light generating elements or lamps, such as light emitting diodes (LEDs) and/or the tips of the individual optical fibers of a fiber bundle. Alternatively, principal surface 1120 of structure 1100 may have a plurality of holes or apertures therein, and one or more backlight lamps, which may include reflectors and/or diffusers, may be provided for passing lighting through the holes to form the plurality of first light sources 1200 which project light onto the cornea of eye 100. Other arrangements are possible.

In another embodiment, structure 1100 is omitted from system 1000, and the first light sources 1200 may be independently suspended (e.g., as separate optical fibers) to form a group of first light sources 1200 arranged around a central axis, the group being separated from the axis by a radial distance defining an aperture in the group (corresponding generally to the aperture 1140 in the structure 1100 illustrated in FIG. 1A).

In one embodiment, second light sources 1300 comprise a plurality of lamps, such as LEDs or optical fiber tips. Alternatively, second light sources 1300 may comprise a plurality of holes or apertures in a surface that are illuminated by one or more backlight lamps with reflectors and/or diffusers.

In one embodiment, second light sources 1300 are located off the central optical axis 1002 of system 1000, and light from second light sources 1300 is directed toward optical element 1740 by third beamsplitter 1760. Alternatively, second light sources 1300 may comprise a plurality of lamps disposed on the structure around the aperture 1780, perpendicular to the optical axis 1002.

Beneficially, each of the second light sources 1300 is located approximately one focal length, f, away from optical element 1740.

Detector array 1400 comprises a plurality of light detecting elements arranged in a two dimensional array. In one embodiment, detector array 1400 comprises such a charge-coupled device (CCD), such as may be found in a video camera. However, other arrangements such as a CMOS array, or another electronic photosensitive device, may be employed instead. Beneficially, the video output signal(s) of detector array 1400 are provided to processor 1410 which processes these output signals as described in greater detail below.

Beneficially, lamp 1520 of third light source 1500 is an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 1550 is a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

Optical element 1740 has an object side (e.g., towards eye 100) and an image side (e.g., towards detector 1400). Optical element 1740 defines an object space located on the object side a finite distance from the optical element, and an image space conjugate the object space. First light sources 1200 are located an optically finite distance from the object space, and second light sources 1300 are located at an optical infinity with respect to the object space. Optical element 1740 is configured to provide an image within the image space when a reflective surface, such as a cornea, is disposed within the object space. Optical element 1740 has a focal length, f, that is adapted to project collimated light from each of the second light sources 1300 through the opening or aperture 1140 of structure 1100 (or through the aperture defined by the group of first light sources 1200, when structure 1100 is omitted) onto the cornea of eye 100.

Beneficially, system 1000 includes both corneal topographer 1010 for measuring the surface of the eye 100 and wavefront analyzer 1020 for measuring ocular aberrations of the total ocular system of the eye 100. More specifically, system 1000 can be considered to comprise six major subsystems: (1) Iris Image; (2) a Fixation Target; (3) a Probe Beam Source; (4) a Wavefront Sensor; (5) a Placido-type Light Source Array; and (6) and Helmholtz Sources.

Important aspects of system 1000 will be better appreciated from an explanation of the operation thereof.

Figure 1B:
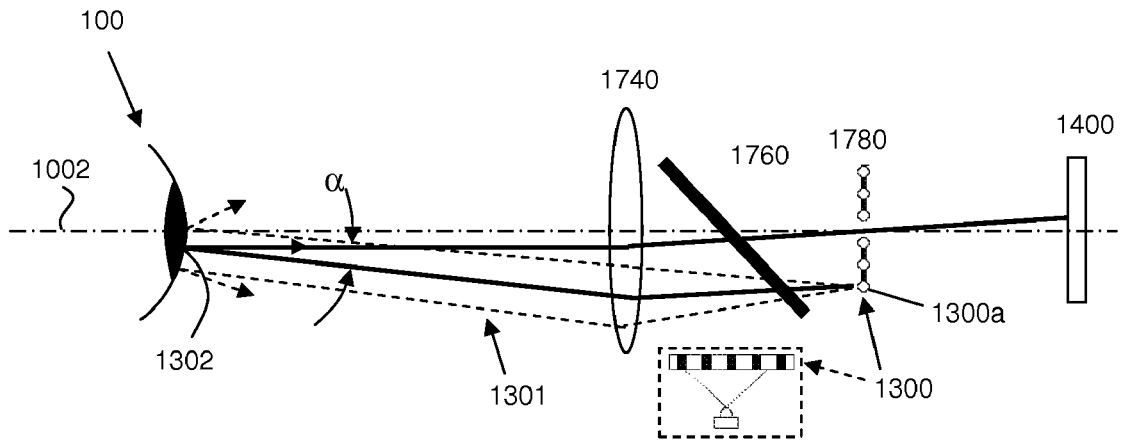
FIGS. 1B-1D illustrate how corneal topography may be measured using first and second light sources in the system of FIG. 1A

Referring to FIG. 1B, which for clarity illustrates only selected elements of the system 1000, operation of the second (central) light sources 1300 may be illustrated. FIG. 1B illustrates how second light sources 1300 may be located optionally either off the central optical axis 1002 of system 1000, or around aperture 1780. The effect of the arrangement of second light sources 1300 insures that light from each of the second light sources 1300 exiting optical element 1740 is collimated as it travels toward the corneal surface and makes an angle α to optical axis 1002 that is the arc tangent of the ratio of the focal length, f, of optical element 1740 and the radial distance of the particular light source 1300 from optical axis 1002, i.e. the center of the aperture 1140.

FIG. 1B illustrates a bundle of light rays from one second light source 1300 in the case where second light sources 1300 are located around the aperture 1780. Within the bundle of rays shown in FIG. 1B, one of the rays (solid line) intersects the corneal surface such that the angle between the surface normal and optical axis 1002 is equal to about α/2. This ray is reflected so that it is parallel to the optical axis 1002, and passes through aperture 1140. This ray makes its way back through optical element 1740 and aperture 1780 onto detector array 1400 to form an image of second light sources 1300 corresponding to its reflected location off the cornea of the eye 100. It will be appreciated that this ray is representative of a small bundle of rays that make it through optical system 1700 and onto detector array 1400, all of which will focus to substantially the same location on detector array 1400. Other rays (dotted lines in FIG. 1B) which impinge the cornea at other locations are scattered in other directions that do not make it through optical system 1700, and accordingly are not imaged onto detector array 1400. Light from each of the remaining second light sources 1300 is collimated at a different angle to central axis 1002 that depends on its distance therefrom. Thus, each of the second light sources 1300 is imaged or mapped to a location on detector array 1400 that may be correlated to a particular reflection location on the cornea of eye 100 and/or the shape of the cornea.

System 1000 employs second light sources 1300 that may be configured according to the Helmholtz principle. In such embodiments, the second light sources 1300 are located at optical infinity with respect to eye 100. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has second light sources 1300 at optical infinity and the telecentric observing system so that detector array 1400 is also optically at an infinite distance from the images of the sources formed by the cornea. Naturally such a measurement system is insensitive to axial misalignment of the corneal surface with respect to the instrument.

Aperture (or stop) 1780 influences the operation of system 1000 in several ways.

First, the size of aperture 1780 sets the solid angle of rays that can be accepted and passed to detector array 1400. This solid angle in turn sets the area of the corneal surface that is sampled by any given light source spot. This may be understood by thinking of the image of a given light source to be located as a virtual image posterior to the corneal surface. Projecting forward from this spot image is a cone of rays; the solid angle that the detector can 'see'. The intersection of this cone with the cornea surface defines the area of that surface sampled by the light source spot. So setting the size of aperture 1780 localizes the area of the cornea that a given light source samples.

Second, because the sampled area size is set by the size of aperture 1780, it sets the amount of light that any single light source spot deposits on detector array 1400. Thus if aperture 1780 is made too small, the spots images are too dim.

Third, the size of aperture 1780 sets the depth of focus of the detector system. If aperture 1780 is too large and the virtual images created by the cornea lie in different planes due to the fact that the power of the cornea, i.e. its curvature, is different in different areas, it becomes hard to get all images in sharp enough focus on detector array 1400 to achieve good image processing results. This can be a problem when measuring a case of keratoconus.

Figure 1C:
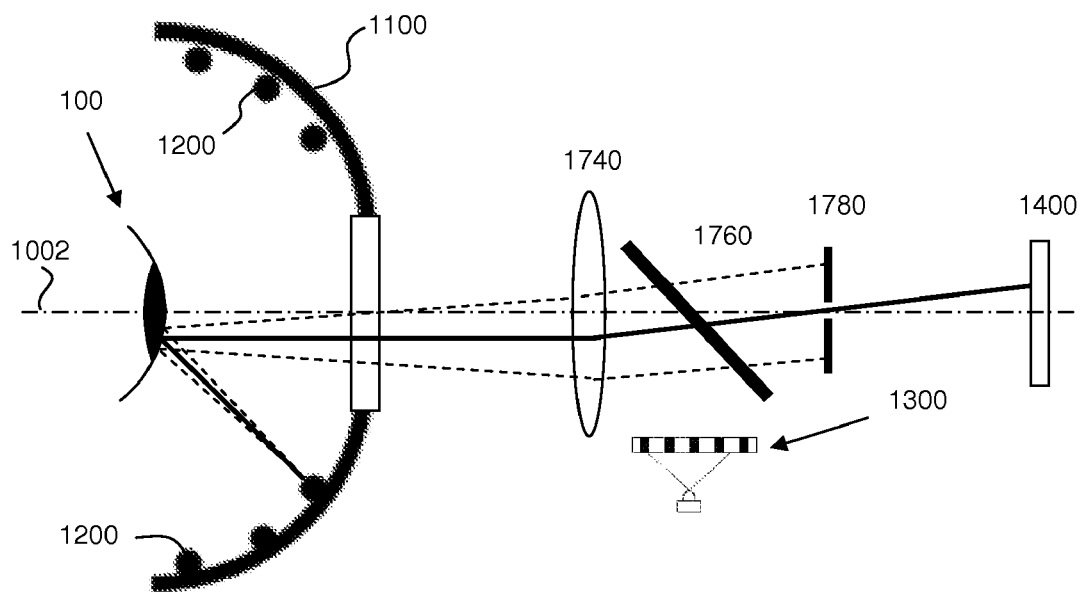

Referring to FIG. 1C, which for clarity illustrates only selected elements of the system 1000, operation of the first (peripheral) light sources 1200 may be illustrated. As shown in FIG. 1C, first light sources 1200 illuminate the cornea of eye 100. A ray (solid line) from one of the first light sources 1200 is reflected by the cornea and passes through optical system 1700 (including aperture 1780) to appear as a light spot on detector array 1400. It will be appreciated that this ray is representative of a small bundle of rays that make it through optical system 1700 and onto detector array 1400, all of which will focus to substantially the same location on detector array 1400. Other rays (e.g., those indicated by the dotted lines in FIG. 1C) from that first light source 1200 are either blocked by the aperture 1780 or are otherwise scatter so as to not pass through the optical system 1700. In similar fashion, light from the other first light sources 1200 are imaged onto detector array 1400 such that each one of first light sources 1200 is imaged or mapped to a location on detector array 1400 that may be correlated to a particular reflection location on the cornea of eye 100 and/or the shape of the cornea. Thus, detector array 1400 detects the light spots projected thereon and provides corresponding output signals to processor 1410. Processor 1410 determines the locations and/or shape of the light spots on detector array 1400, and compares these locations and/or shapes to those expected for a standard or model cornea, thereby allowing processor 1410 to determine the corneal topography. Alternatively, other ways of processing the spot images on detector array 1400 may be used to determine the corneal topography of eye 100, or other information related to the characterization of eye 100.

Figure 1D:
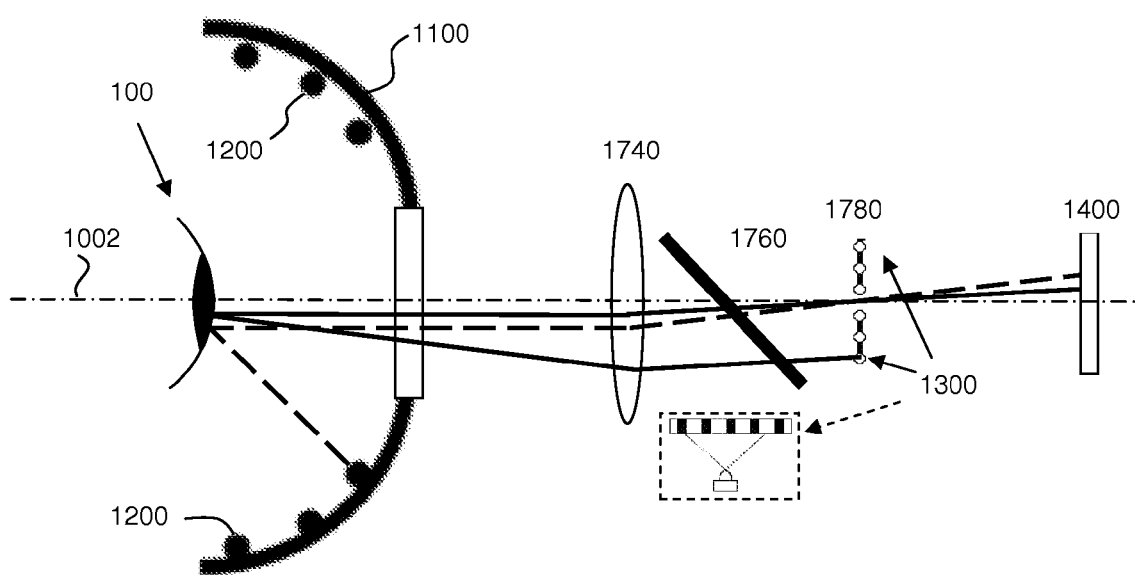

With additional reference to FIG. 1D, the operation of the topographer portion of system 1000 may be illustrated based on the combined use of first and second light sources 1200, 1300. In general, the images of first light sources 1200 that appear on detector array 1400 emanate from an outer region of the surface of the cornea, and the images of second light sources 1300 that appear on detector array 1400 emanate from a central or paraxial region of the surface of the cornea. Accordingly, even though information about the central region of the corneal surface (e.g., surface curvature) cannot be determined from the images of first light sources 1200 on detector array 1400, such information can be determined from the images of second light sources 1300 on detector array 1400.

So, as illustrated in FIG. 1D, detector array 1400 detects the light spots projected thereon from both second light sources 1300 (detected at a central portion of detector array 1400) and first light sources 1200 (detected at a peripheral portion of detector array 1400) and provides corresponding output signals to processor 1410. Processor 1410 determines the locations and/or shapes of the light spots on detector array 1400, and compares these locations and/or shapes to those expected based for a standard or model cornea, thereby allowing processor 1410 to determine the corneal topography of eye 100. Accordingly, the topography of the entire corneal surface can be characterized by system 1000 without a "hole" or missing data from the central corneal region.

Meanwhile, the presence of the aperture or opening in the middle of the group of first light sources 1200 (e.g., aperture 1140 in principal surface 1120 of structure 1100) allows system 1000 to provide a probe beam into eye 100 to characterize its total ocular aberrations. Accordingly, as described in greater detail below, third light source 1500 supplies a probe beam through polarizing beamsplitter 1620 and adjustable telescope 1640 to first beamsplitter 1720 of optical system 1700. First beamsplitter 1720 directs the probe beam through aperture 1140 to eye 100. Beneficially, light from the probe beam is scattered from the retina of eye 100, and at least a portion of the scattered light passes back through aperture 1140 to first beamsplitter 1720. First beamsplitter 1720 directs the scattered light through adjustable telescope 1640 and polarizing beamsplitter 1620 to wavefront sensor 1550.

Wavefront sensor 1550 outputs signals to processor 1410 which uses the signals to determine ocular aberrations of eye 100. Beneficially, processor 1410 is able to better characterize eye 100 by considering the corneal topography of eye 100, which may also be determined by processor 1410 based on outputs of detector array 1400, as explained above.

Figure 2:
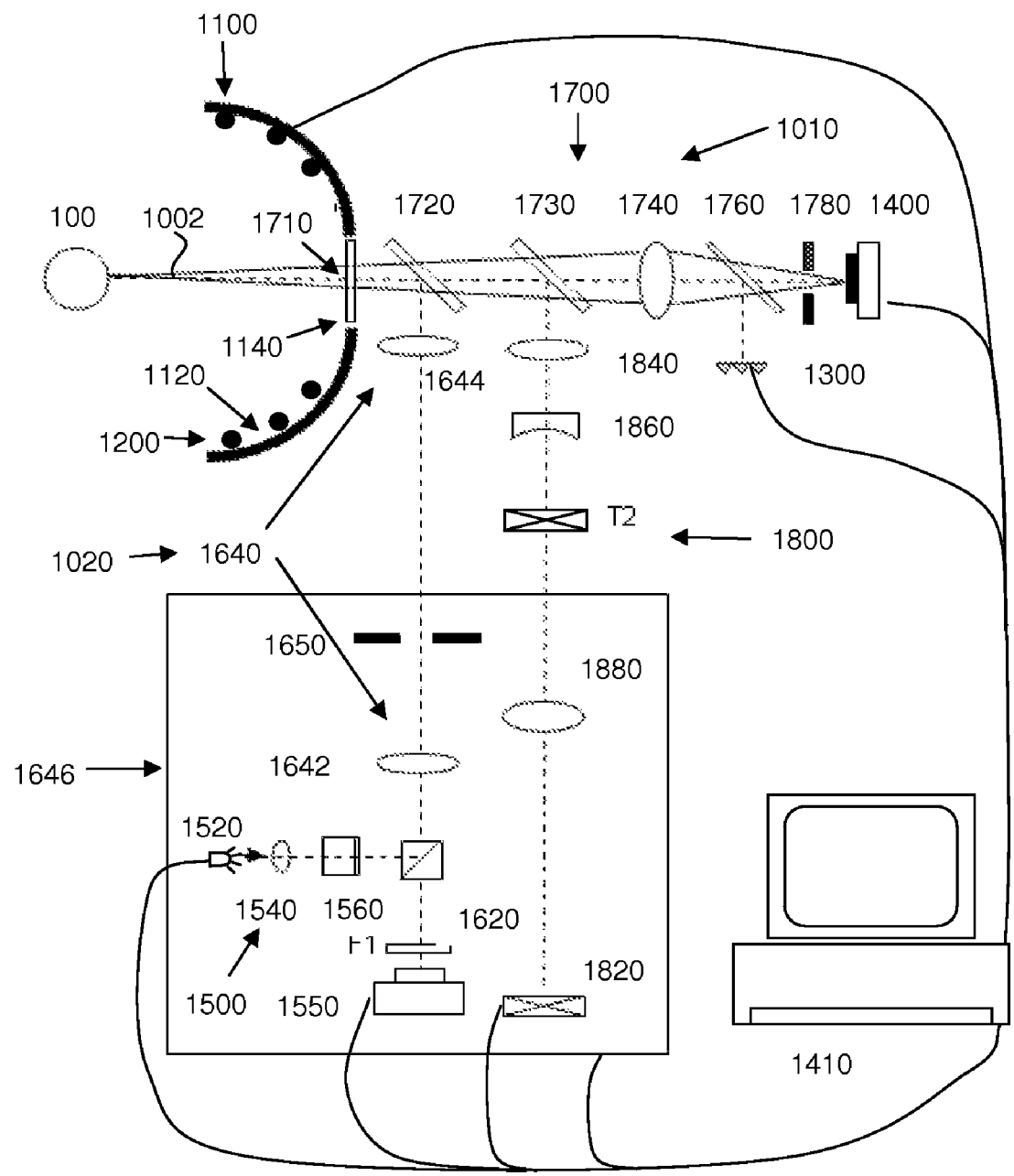
FIG. 2 illustrates imaging rays for an eye's iris in the system of FIG. 1A.

FIG. 2 illustrates imaging rays for an iris of eye 100 in system 1000 of FIG. 1A.

Rays drawn in FIG. 2 show the imaging condition between eye 100 and detector array 1400. In normal use, an operator will adjust a position or alignment of system 1000 in XY and Z directions to align the patient according to the image detector array 1400. In one embodiment, eye 100 is illuminated with infrared light. In this way, the wavefront obtained by wavefront sensor 1550 will be registered to the image from detector array 1400.

The image that the operator sees is the iris of eye 100. The cornea generally magnifies and slightly displaces the image from the physical location of the iris. So the alignment that is done is actually to the entrance pupil of the eye. This is generally the desired condition for wavefront sensing and iris registration.

Beneficially, system 1000 includes fixation target 1800 for the patient to view. Fixation target system 1800 is used to control the patient's accommodation, because it is often desired to measure the refraction and wavefront aberrations when eye 100 is focused at its far point (e.g., because LASIK treatments are primarily based on this).

Figure 3:
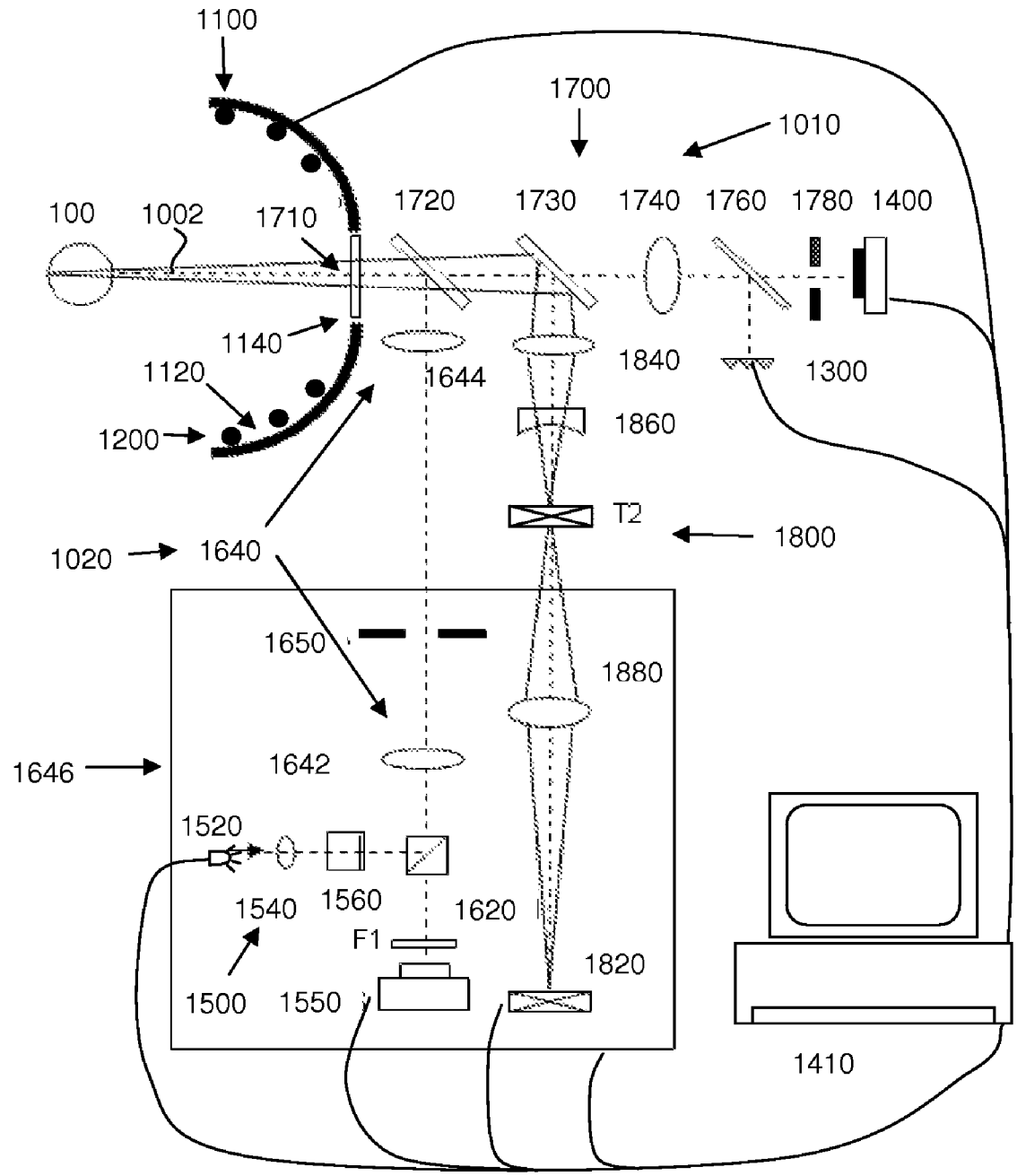
FIG. 3 illustrates rays for a fixation target in the system of FIG. 1A.

FIG. 3 illustrates rays for a fixation target system 1800 in system 1000 of FIG. 1.

Light originates from the light source 1820. This could be a back lit reticule or an LCD microdisplay. Lens 1840 collects the light and forms an aerial image T2. This aerial image is the one that the patient views. Rays drawn from T1 to T2 indicate this imaging condition. Lens 1840 may be used to magnify the aerial image to the appropriate size and also to provide mechanical clearance as the movable stage or platform 1646 moves.

FIG. 3 shows the rays from the retina of eye 100 to T2. This indicates a condition when the target T2 would appear in focus to the patient. This state would tend to induce accommodation and would not be desired for measuring the far point of the eye.

From this condition, movable stage or platform 1646 is moved down until eye 100 can no longer focus the target T2 and the target T2 appears fuzzy. This relaxes the patient's accommodation until the far point is reached, at which point the refraction and aberrations of eye 100 are measured.

Beneficially, the increments of motion of movable stage or platform 1646 are made relatively small and the motions are relatively slow (compared to how far and fast a stage can be made to move) so that eye 100 can follow the target T2. At each stage location, the wavefront and refraction of eye 100 is measured. When the eye's refractive state no longer changes as the target T2 moves farther out, the far point of eye 100 has been reached. The last measurement is the refraction and wavefront of eye 100 at the far point.

FIG. 3 shows that the patient views the fixation target T2 through lenses 1860 and 1880. Two lenses are used in order to form a retrofocus lens so that the principal plane of the lens group can be made to coincide with the principal plane of lens 1644 of wavefront analyzer 1020. This makes it so the vergences on the path of wavefront sensor 1550 and the fixation target path match for all positions of movable stage 1646, which is a necessary condition for the fogging function to work properly.

FIG. 4 illustrates rays for a probe beam employed in system 1000 of FIG. 1 for wavefront analysis.

Beneficially, in system 1000 the refraction and aberrations of eye 100 are measured using light that is injected into eye 100 and that scatters off the eye's retina.

In FIG. 4 rays leave lamp 1520 and are collimated by lens 1540. The light passes through light source polarizing beam splitter 1560. The light entering light source polarizing beam splitter 1560 is partially polarized. Light source polarizing beam splitter 1560 reflects light having a first, S, polarization, and transmits light having a second, P, polarization so the exiting light is 100% linearly polarized. In this case, S and P refer to polarization directions relative to the hypotenuse in light source polarizing beam splitter 1560.

Light from light source polarizing beam splitter 1560 enters polarizing beamsplitter 1620. The hypotenuse of polarizing beamsplitter 1620 is rotated 90 degrees relative to the hypotenuse of light source polarizing beam splitter 1560 so the light is now S polarized relative the hypotenuse of polarizing beamsplitter 1620 and therefore the light reflects upwards.

The light from polarizing beamsplitter 1620 travels upward and passes through telescope 1640 comprising lenses 1642 and 1644. Back reflections off of lenses 1642 and 1644 will be S polarized so they will reflect off polarizing beamsplitter 1620 and be directed toward lamp 1520. In the figure, the polarization is perpendicular to the plane of the paper. This reflection prevents back reflections off 1642 and 1644 from reaching wavefront sensor 1550. In practice, the reflectivities of 1642 and 1644 should be less than 0.5% for no back reflections to appear on wavefront sensor 1550.

After passing through lens 1644, the light reflects off first beamsplitter 1720, retaining its S polarization, and then travels through quarter wave plate 1710. Quarter wave plate 1710 converts the light to circular polarization. The light then travels through aperture 1140 in principal surface 1120 of structure 1100 to eye 100. Beneficially, the beam diameter on the cornea is between 1 and 2 mm. Then the light travels through the cornea and focuses onto the retina of eye 100.

The focused spot of light becomes a light source that is used to characterize eye 100 with wavefront sensor 1550.

Figure 5:
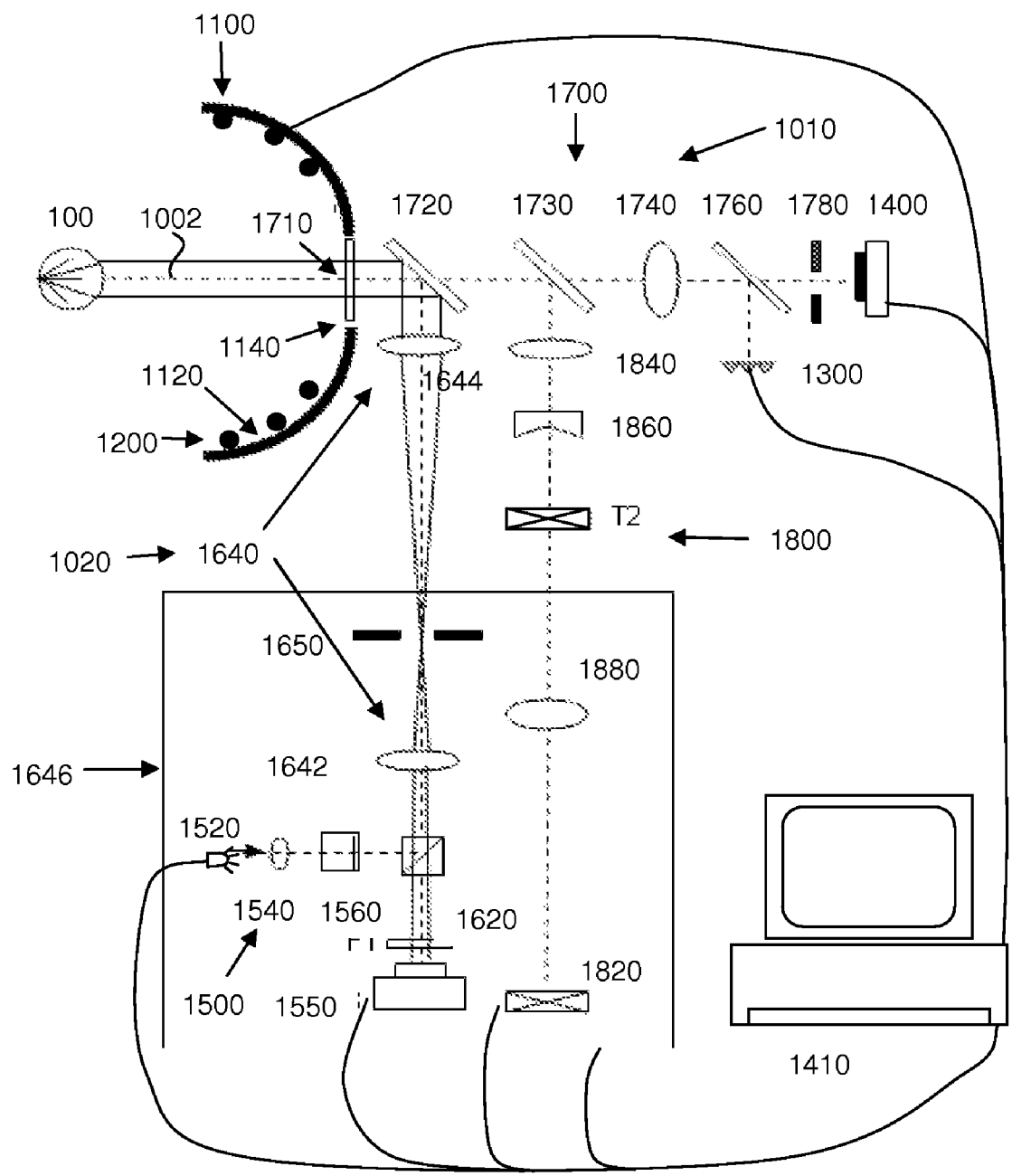
FIG. 5 illustrates rays for a wavefront sensor in the system of FIG. 1A.

FIG. 5 illustrates rays from the focused spot on the retina that to the wavefront sensor 1550 in system 1000 of FIG. 1.

Light from the probe beam that impinges on the retina of eye 100 scatters in various directions. Some of the light travels back out of the cornea and to the wavefront sensor 1550. Measurements indicate that of the light sent into the cornea, only about 1/4000th is reflected back out. This light then travels as a semi-collimated beam back towards system 1000.

Upon scattering, about 90% of the light retains its polarization. So the light traveling back towards system 1000 is substantially still circularly polarized. The light then travels through aperture 1140 in principal surface 1120 of structure 1100, through quarterwave plate 1710, and is converted back to linear polarization. Quarterwave plate 1710 converts the polarization of the light from the eye's retina so that it is P polarized, in contrast to probe beam received from third light source 1500 having the S polarization. This P polarized light then reflects off of first beamsplitter 1720, travels through telescope 1640, and then reaches polarizing beamsplitter 1620. Since the light is now P polarized relative the hypotenuse of polarizing beamsplitter 1620, the beam is transmitted and then continues onto wavefront sensor 1550.

When wavefront sensor 1550 is a Shack-Hartmann sensor, the light is collected by the lenslet array in wavefront sensor 1550 and an image of spots appears on the detector array (e.g., CCD) in wavefront sensor 1550. This image is then provided to processor 1410 and analyzed to compute the refraction and aberrations of eye 100.

Figure 6:
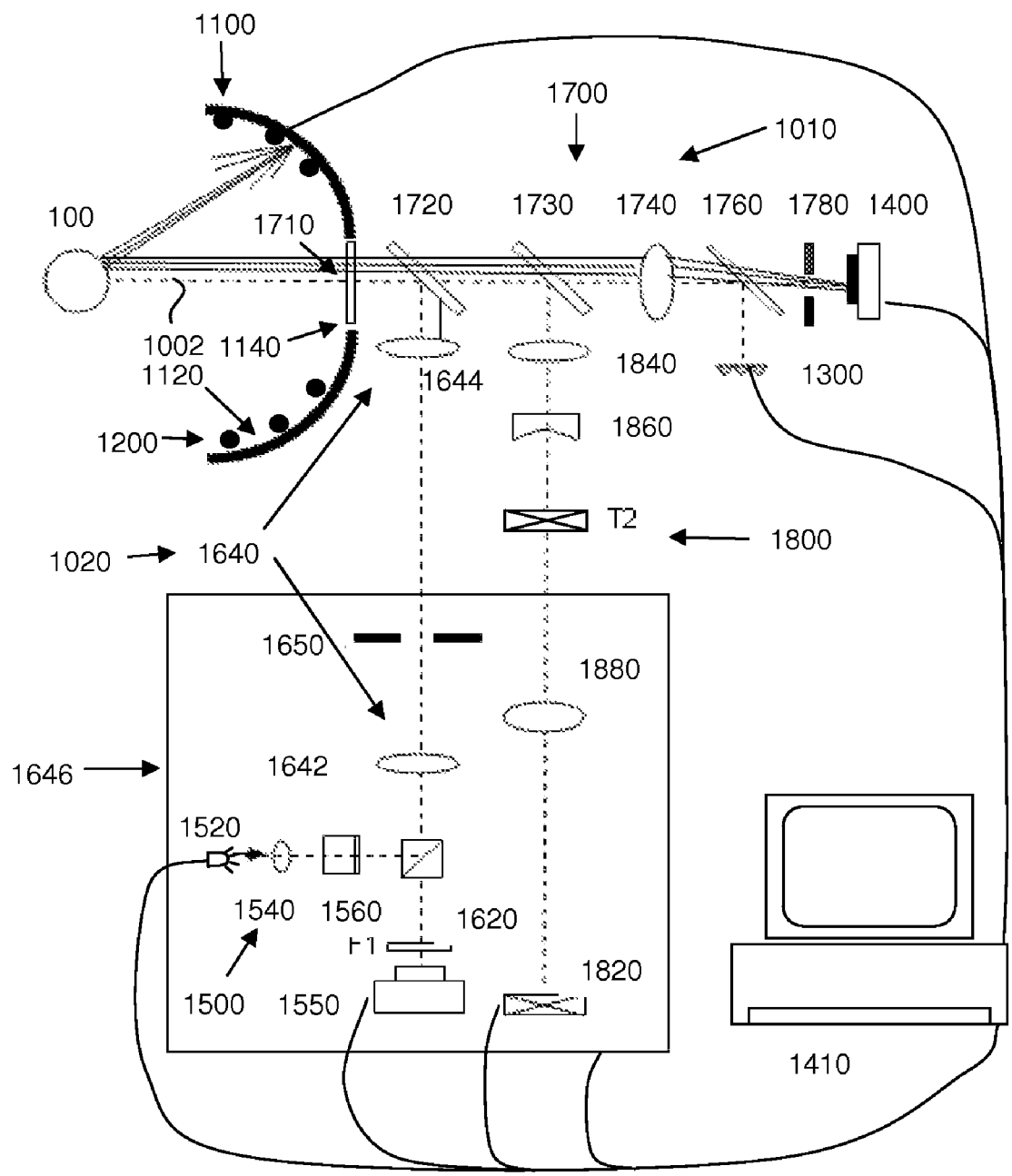
FIG. 6 illustrates corneal topography rays in the system of FIG. 1A.

FIG. 6 illustrates corneal topography rays in system 1000 of FIG. 1.

System 1000 measures the curvature and shape of the cornea. Light for this measurement is provided by first light sources 1200. In FIG. 6, first light sources 1200 are provided on principal surface 1100 of structure 1100, although as explained above in one embodiment, structure 1100 may be omitted and the group of first light sources 1200 is arranged around central optical axis 1002, with the group being separated from the axis by a radial distance defining an aperture in the group. In one embodiment, structure 1100 is a conical frustum which is backlit with one or more lamps, and first light sources 1200 comprise a pattern of holes in principal surface 1100 through which the backlit light passes. Light from each of first light sources 1200 forms a virtual image behind the cornea. That virtual image is converted into a real image appearing as a light spot on detector array 1400 by optical element (e.g., lens) 1740. The location of each spot depends on the local curvature at a very small section of the cornea.

Accordingly, the light spots from the cornea form a pattern on detector array 1400. The resulting pattern is analyzed by processor 1410 of system 1200 to determine the base curvature and shape of the cornea.

In FIG. 6, light rays are shown emanating in various directions from one of light sources 1200. Some of the light will reflect off the cornea and travel back to system 1000. In FIG. 6, only those rays that reach detector array 1400 are shown drawn completely.

Beneficially, the arrangement in the embodiment shown as system 1000 is telecentric. A convenient definition of telecentricity is that for each image point, the chief ray is traveling parallel to the system's optical axis 1002 after the light reflects from the cornea. The chief ray is the one that travels through the center of aperture 1780. In FIG. 6, aperture 1780 may be a telecentric stop located one focal length behind optical element 1740.

The diameter of the telecentric aperture 1780 may be selected to determine how much light from any particular spot of light is sampled. If aperture 1780 is made too large, there may be too much overlap between the individual images of the individual sources of first and second light sources 1200, 1300 for accurate calculation of corneal shape. However, if aperture 1780 is made too small, not enough light reaches detector array 1400 for a usable image to form. In one embodiment, a practical size for aperture 1780 is between 1 and 4 mm.

Beneficially, aperture 1780 may be selected such that it is the only aperture that restricts how much light reaches detector array 1400. Deviations from that can result in departures from telecentricity and consequent miscalculations of the shape of the cornea.

Figure 7:
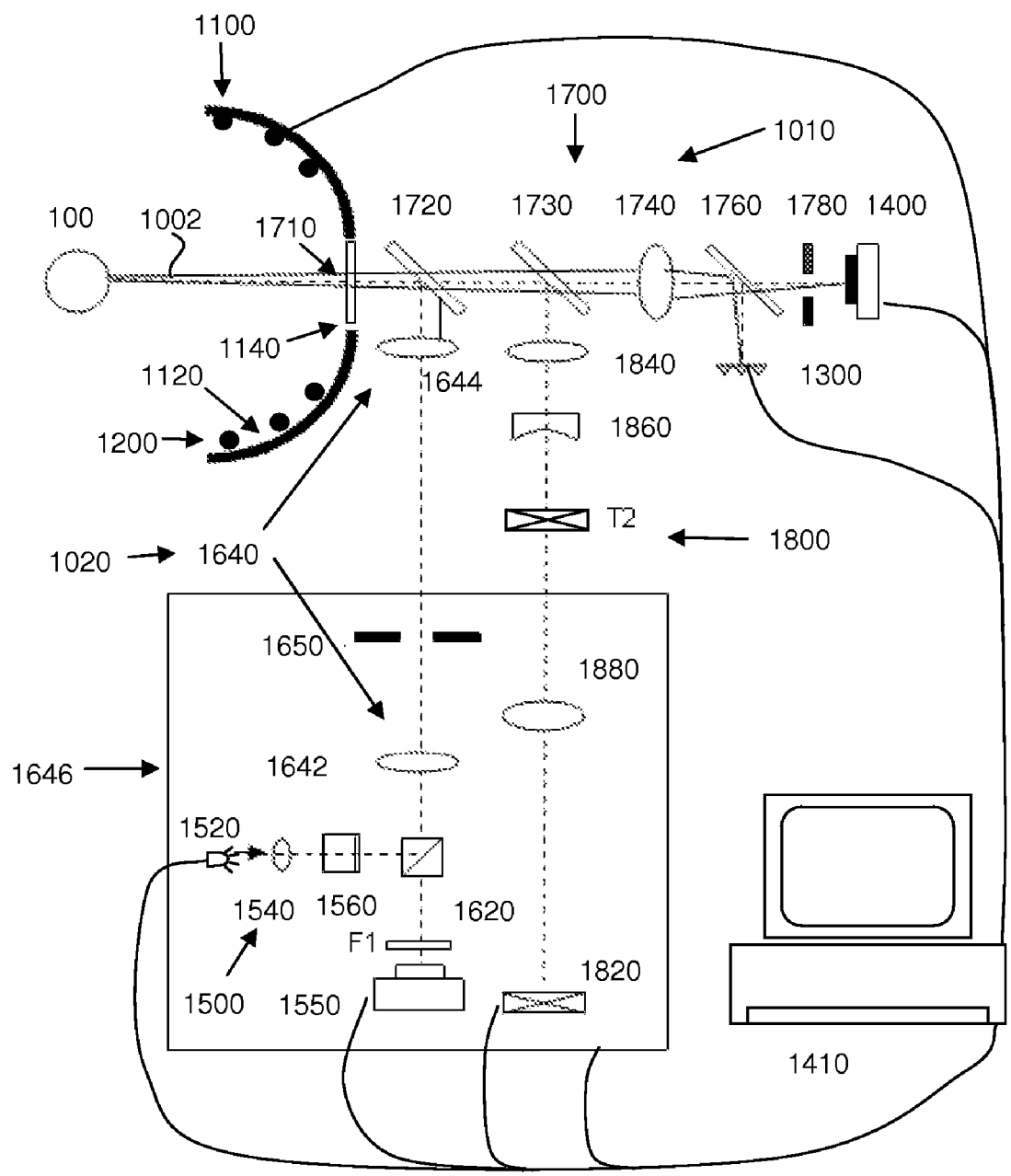
FIG. 7 illustrates operating principals of a set of central light sources included in the system of FIG. 1A.

FIG. 7 illustrates rays from second light sources 1300 in the system 1000 of FIG. 1.

Second light sources 1300 solve a problem that plagues conventional corneal topographers. As noted above, with a conventional corneal topographer it is difficult to make a measurement of the corneal shape near the optical axis of the instrument. This is because any light source that would illuminate the center of the cornea would also block any optical path from the cornea back to the detector array. This is unfortunate because the center of the cornea is the region of most interest for its impact on visual performance.

FIG. 7 illustrates how second light sources 1300 solve this problem.

In FIG. 7, a grid pattern of lighted spots is placed at the location marked 1300 to indicate the second light sources. For instance, a 3× grid may be used. This grid is placed in an optical path one focal length, f, away from optical element 1740.

Second light sources 1300 generate light that passes through optical element 1740 and travels as collimated light beams to the cornea. The light reflects off the cornea and diverges after the reflection. Some of the light travels back through optical element 1740. A small bundle of this light then passes through aperture 1780 onto detector array 1400. The aperture 1780 limits the solid angle of rays that are allowed to pass through to detector array 1400. The size of aperture 1780 can be optimized for many parameters; one example being the amount of light from any particular second source point 1300 that gets reflected off the cornea of eye 100 and is sampled on the detector array 1400.

Another way to view this is that the second light sources 1300 each form a virtual image behind the cornea and then that image is relayed onto detector array 1400, similar to the virtual images from first light sources 1200.

As mentioned above, a variety of different shapes may be employed for structure 1100, with various advantages and disadvantages. However, once a shape has been selected for principal surface 1120, the question remains as to the locations where first light sources 1200 should be provided.

Figure 8:
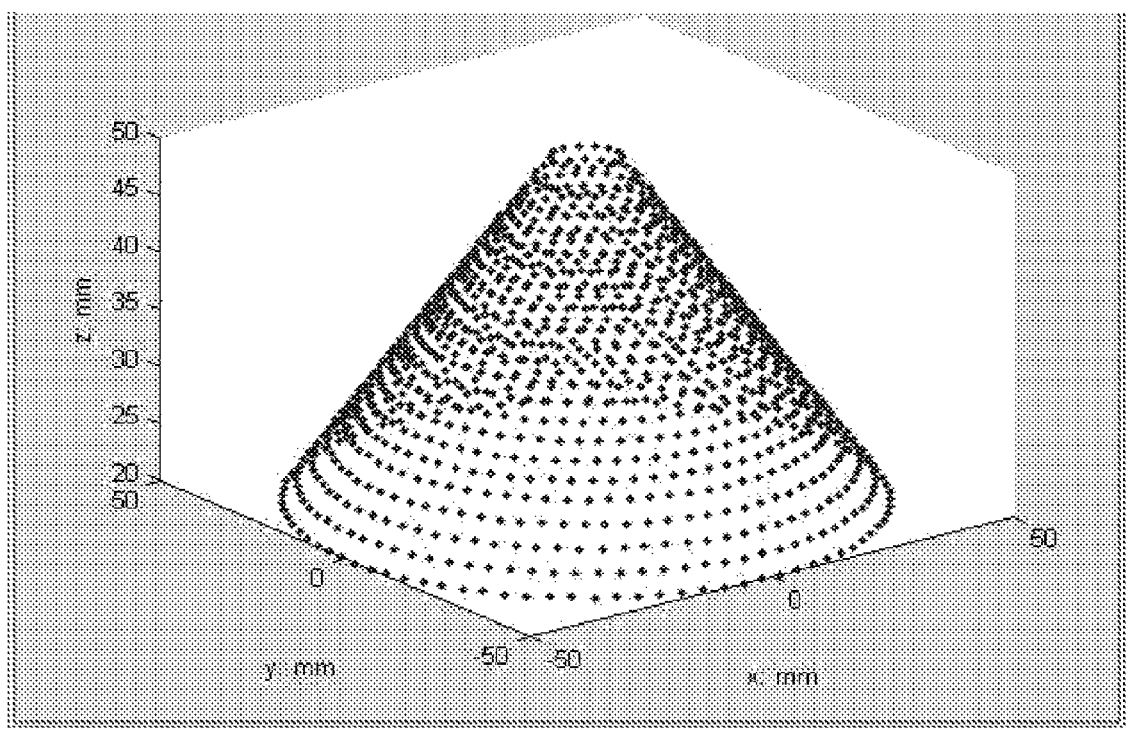
FIG. 8 illustrates a uniform distribution of light sources on the surface of a cone in one embodiment of the system of FIG. 1A.

FIG. 8 illustrates a uniform distribution of first light sources 1200a on the surface 1120a of a conical frustum 1100a in one embodiment of the system of FIG. 1. As before, these first light sources 1200a may be individual lamps, or surface 1120a may be backlit with one or more lamps, and sources 1200a may include holes or apertures in 1120a through which the backlit light passes.

Figure 9:
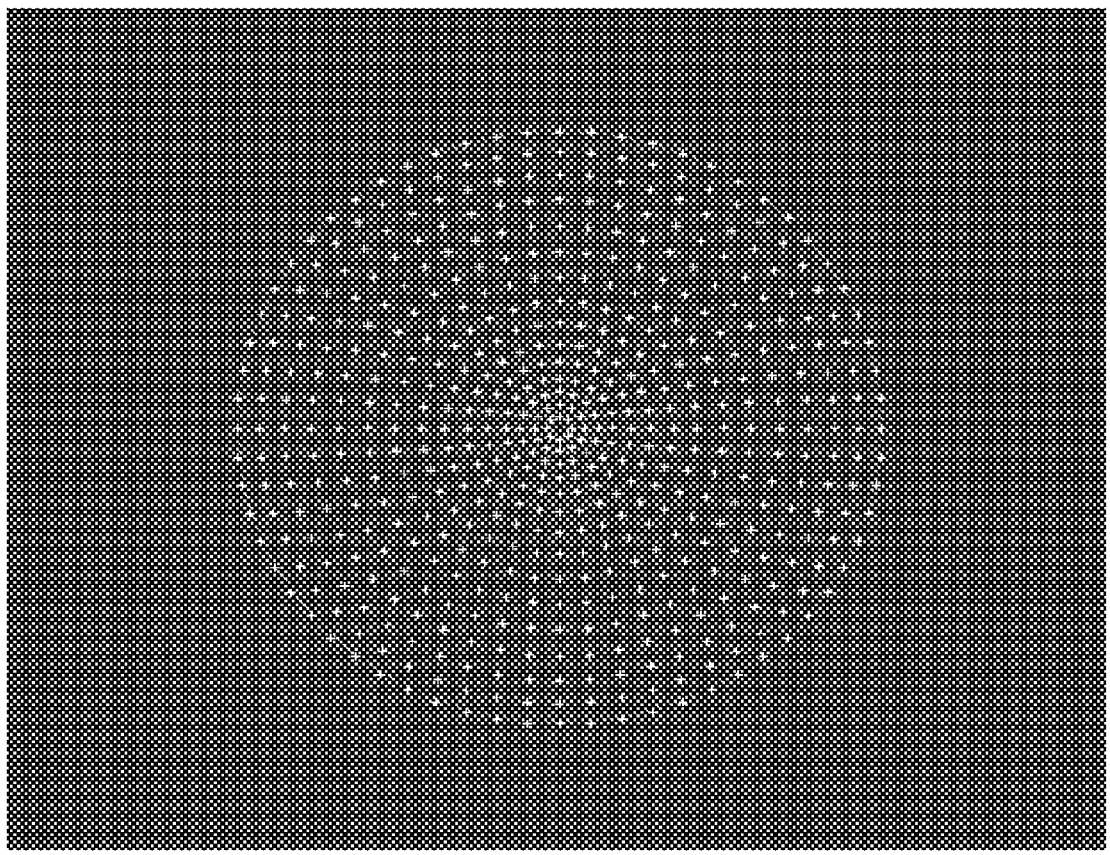
FIG. 9 illustrates a pattern of light spots produced on a detector in the system of FIG. 1 when the light source pattern of FIG. 8 is employed.

FIG. 9 illustrates a pattern of light spots produced on detector array 1400 in the system 1000 of FIG. 1 when the light source pattern of FIG. 8 illuminates a reference object, such as an idealized corneal surface, or a sphere with a radius of curvature (ROC)=7.9 mm, etc. As can be seen in FIG. 8, the light spots from first light sources 1200a are not uniformly spaced or arranged on detector array 1400. This can complicate the calculations which must be performed by processor 1410 of system 1000 to calculate a measured cornea's topography.

Figure 10:
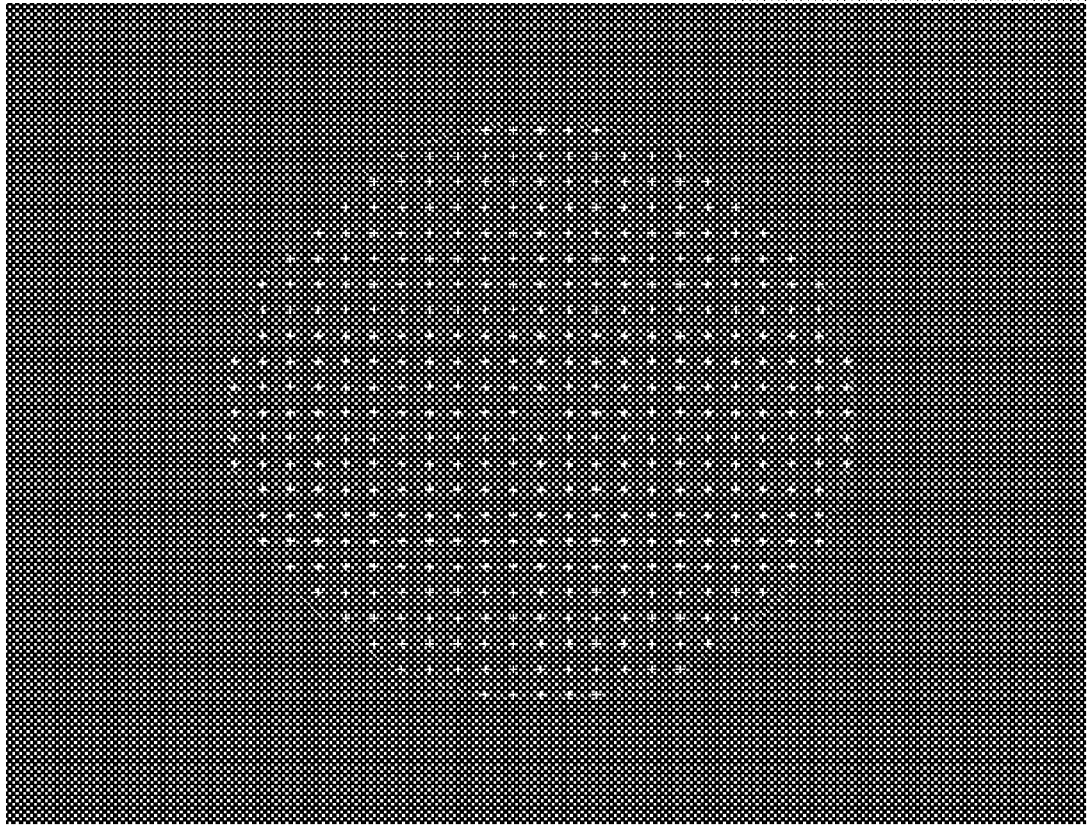
FIG. 10 illustrates a uniform pattern of light spots on a grid on a detector in the system of FIG. 1A.

FIG. 10 illustrates a uniform pattern of light spots on a grid on detector array 1400 in the system 1000 of FIG. 1. The light spots in FIG. 10 are uniformly and evenly spaced on a grid on detector array 1400.

Figure 11:
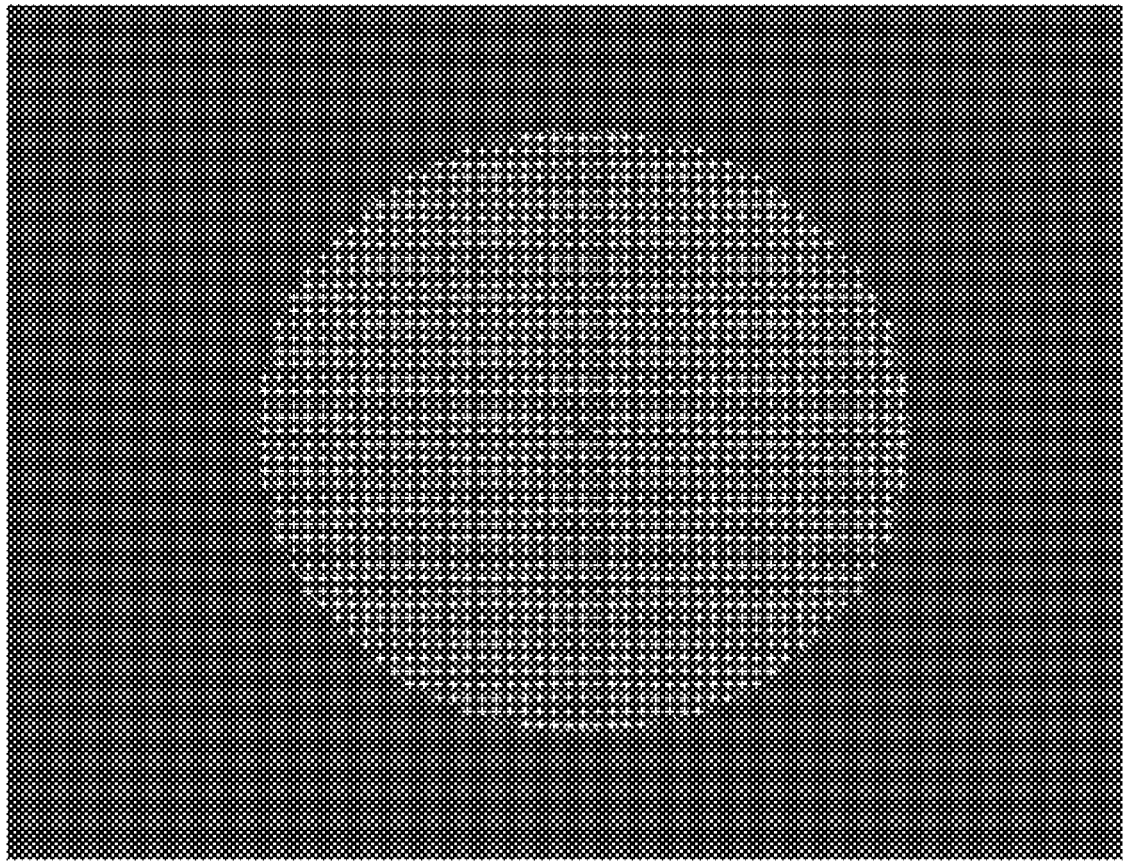
FIG. 11 illustrates another uniform pattern of light spots on a grid on a detector in the system of FIG. 1A.

FIG. 11 illustrates another uniform pattern of light spots on a grid on detector array 1400 in the system 1000 of FIG. 1. The light spots in FIG. 11 are also uniformly and evenly spaced on a grid on detector array 1400, however compared to FIG. 10, there are more light spots and a greater light spot density.

There are several reasons for wanting a uniform grid produced on detector array 1400. If a reference surface (e.g., an idealized cornea, a sphere with ROC=7.9 mm, etc.) could produce the pattern of FIG. 10 or FIG. 11, for example, on detector array 1400, this could facilitate easier reconstruction of the corneal topography, since the expected spots for a "reference eye" will be on a grid, and small deviations might easily lead to simple reconstruction methods. Furthermore, with the spot pattern being close to a grid, the spot location algorithm becomes much simpler and might easily be tackled with a difference image calculated from an image with and without first light sources 1200 turned-on, followed by centroiding algorithms based on predefined areas of interest (AOI). An additional translation calculation might be needed prior to AOI-based centroiding to account for system misalignment.

To calculate the locations of the first light sources 1200, one begins at detector array 1400 with the desired spot separation specified in pixels and propagates rays backwards through the optical system 1700 to the spot locations on an idealized cornea (or retina). Then the locations of the spots on the idealized retina (or sphere) are used to find where on the principal surface 1120 the reflected rays intersect. These intersection locations are where the first light sources 1200 should be provided.

Figure 12:
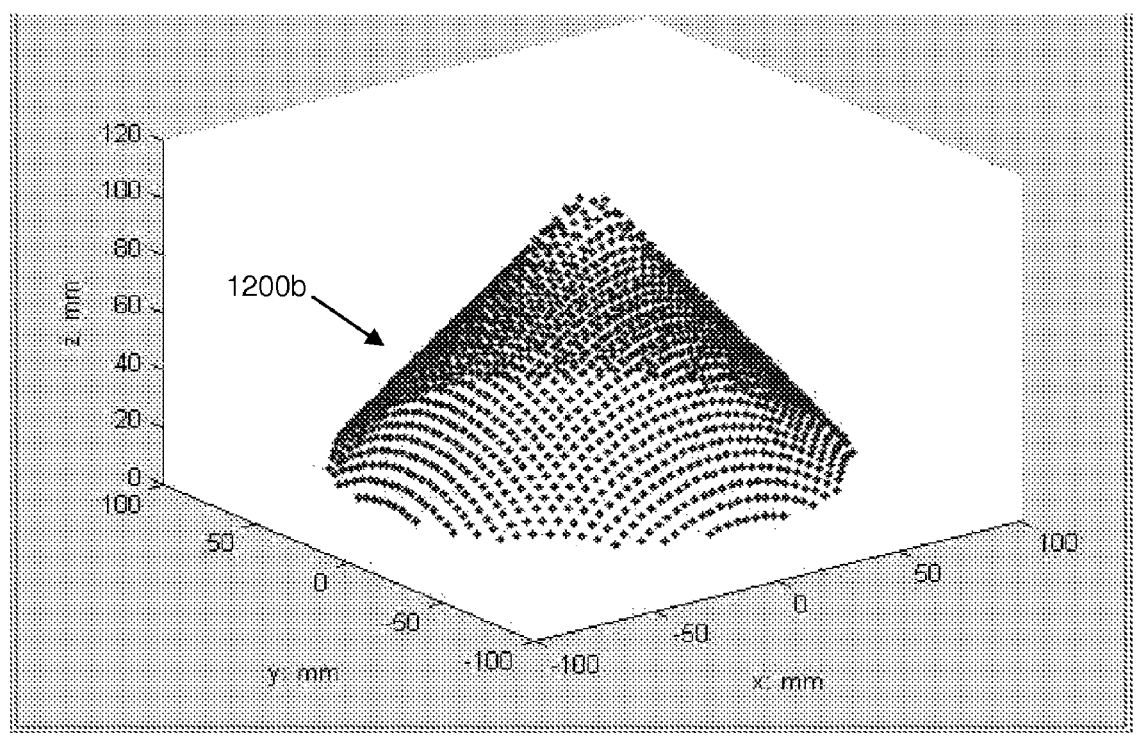
FIG. 12 illustrates a distribution of light sources on the surface of a cone that can produce a uniform pattern of light spots on a grid on a detector in the system of FIG. 1A.
Figure 12A:
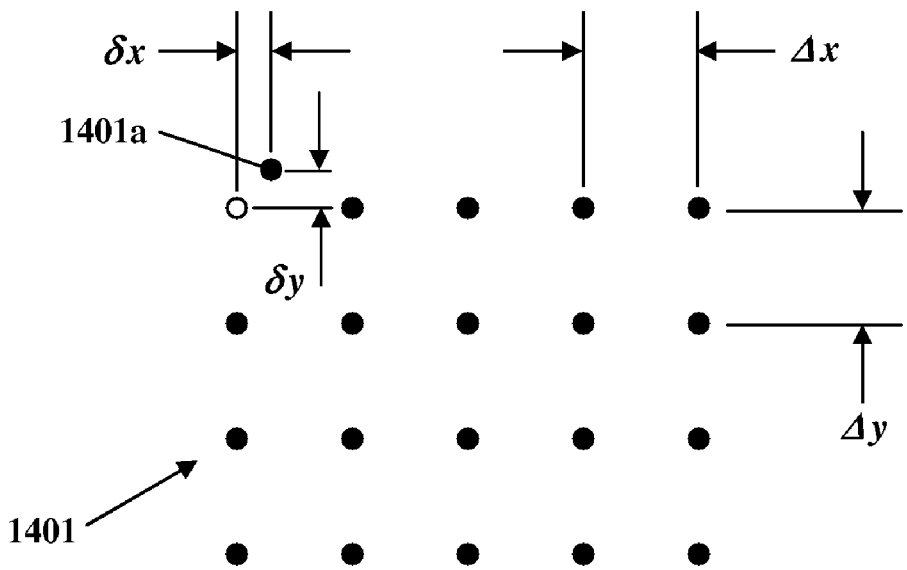
FIG. 12A illustrates a portion of a grid pattern produces by light sources of a corneal topographer according to an embodiment of the present invention.

FIG. 12 illustrates a distribution of first light sources 1200b on the surface 1120a of a conical frustum 1100a that can produce a uniform grid pattern of light spots on a grid on detector array 1400 in the system 1000 of FIG. 1. The inventors have discovered that this type of configuration provides unexpected advantages in processing data to reconstruct the surface of a reference or test object. Specifically, the distribution of first light sources 1200b to both form a conical frustum and produce a grid at an image plane (e.g., the detector array 1400) has been found to produce a large dynamic range. The inventors have used this combination of light distribution properties to produce a system in which the deviation from a uniform grid pattern is only about plus or minus 2% for test surface radius of curvatures ranging from 6 mm to 11 mm. For example, referring to FIG. 12A, a portion of an image formed at the detector array 1400 is shown, where the image comprises a plurality of images 1401 each corresponding to light from an individual light source 1200 that is reflected from the surface 100. In the illustrated embodiment, the images 1401 are in the form of circular spots and form a grid pattern in which the spacing between images is Δx along a horizontal axis and Δy along a vertical axis. A deviation from the uniform grid pattern is shown by an image 1401a, in which the deviation is indicated by the values δx and δy. The deviation of the image 1401a from the uniform grid pattern may be defined as:

$$\sqrt{\delta x^2 \delta y^2}/\sqrt{\Delta x^2 + \Delta y^2}$$

Thus, for the current embodiment, the maximum deviation from a uniform grid pattern for a spherical test surface having a radius of curvatures ranging from 6 mm to 11 mm is only 2%.

Figure 12B:
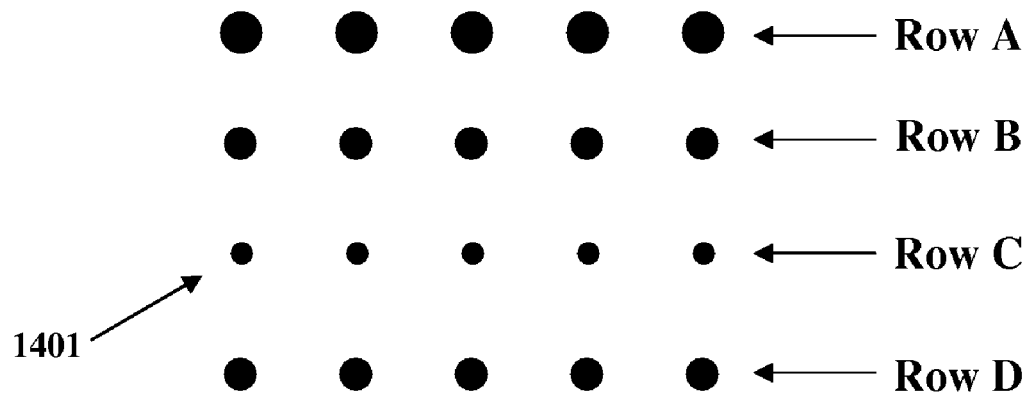
FIG. 12B illustrates a portion of a grid pattern of defocused spot images produces by light sources of a corneal topographer according to an embodiment of the present invention.

Referring to FIG. 12B, the light sources 1200 may be configured so that at least some of the corresponding images 1401 are defocused or blurred. The images in Row C of FIG. 2012B are relatively small and thus have no, or relatively little, defocus or blur on the detector array 1400. By contrast, the images 1401 in Row B and Row D are larger than those in Row C due to a larger amount of defocus or blur, assuming the light sources 1200 all have the same size. The images 1401 in Row A are even larger, and thus are more defocused or blurred than the images 1401 in Rows B, C, or D. The inventors have found that at least some defocus or blurring of the images 1401 advantageously increases the accuracy in reconstructing the shape of the of object 100 based on the images 1401, since each image covers more pixels of the detector array 1400, which allows the center of the image to be determined with greater accuracy. As used herein, the term "defocus" means a separation, along an optical axis of an imaging system, of a detector plane from a best focus of an image that is defocused at the detector plane. As used herein, the term "blur" means an increase in a size of a detected image in a detector plane as compared to a size of the image at a focal plane thereof.

Figure 12C:
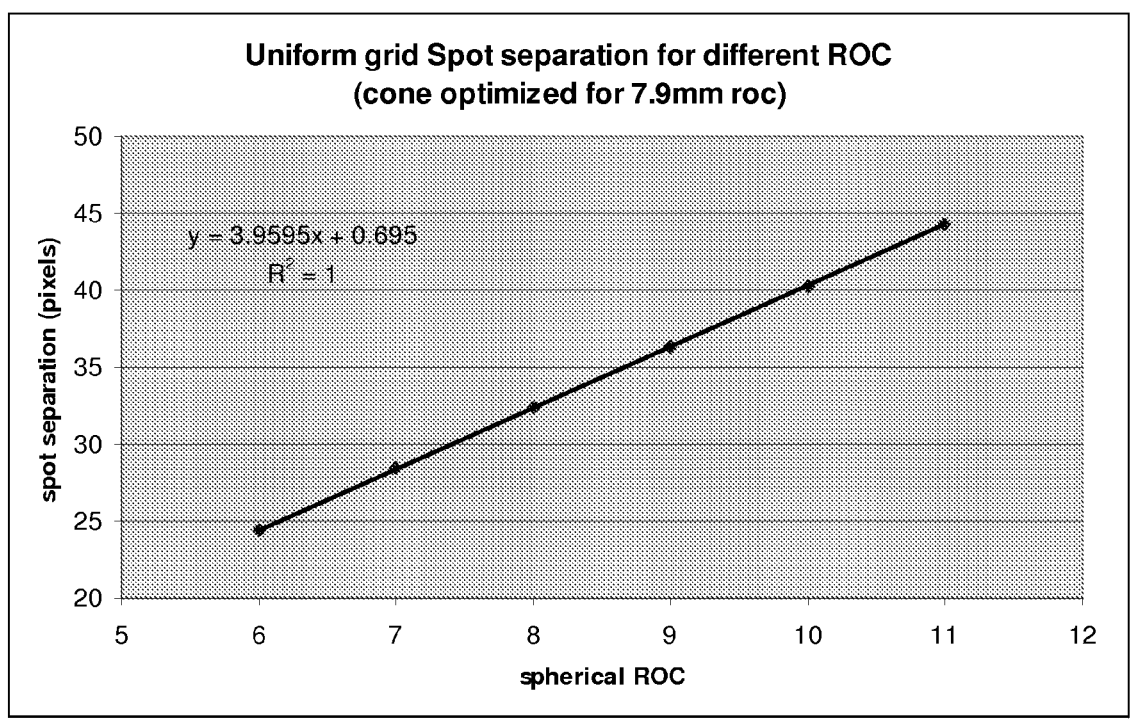
FIG. 12C is a plot showing a linear relationship between an average spacing between spot images in a grid pattern and the radius of curvature of a test object.

The light sources 1200 may by advantageously configured so that the average separation (e.g., average Δx and/or average Δy in FIG. 12A or 12B over the entire detector array 1400) varies linearly with the radius of curvature of an illuminated spherical surface of the test object 100. For example, the light sources 1200 provided by the principal surface 1120 having the shape of a conical frustum may be configured to produce nominally uniform grid patterns in which the average image separation varies according to the linear function shown in FIG. 12C, wherein the radius of curvature of the illuminated test surface 100 varies from 6 mm to 11 mm. The plots below in FIG. 12C show about a 1% P-V deviation in spot uniformity from an ideal grid.

A conventional topographer suffers from a scale ambiguity, whereby it is necessary to know the distance from the instrument to the cornea in order to accurately calculate the base radius of curvature of the cornea unless. That is, if the vertex of a reference surface or test corneal surface is not located at a design corneal vertex plane, for example due to misalignment between the instrument and the cornea, it will result in an error in the calculated radius of curvature of the cornea.

Figure 13:
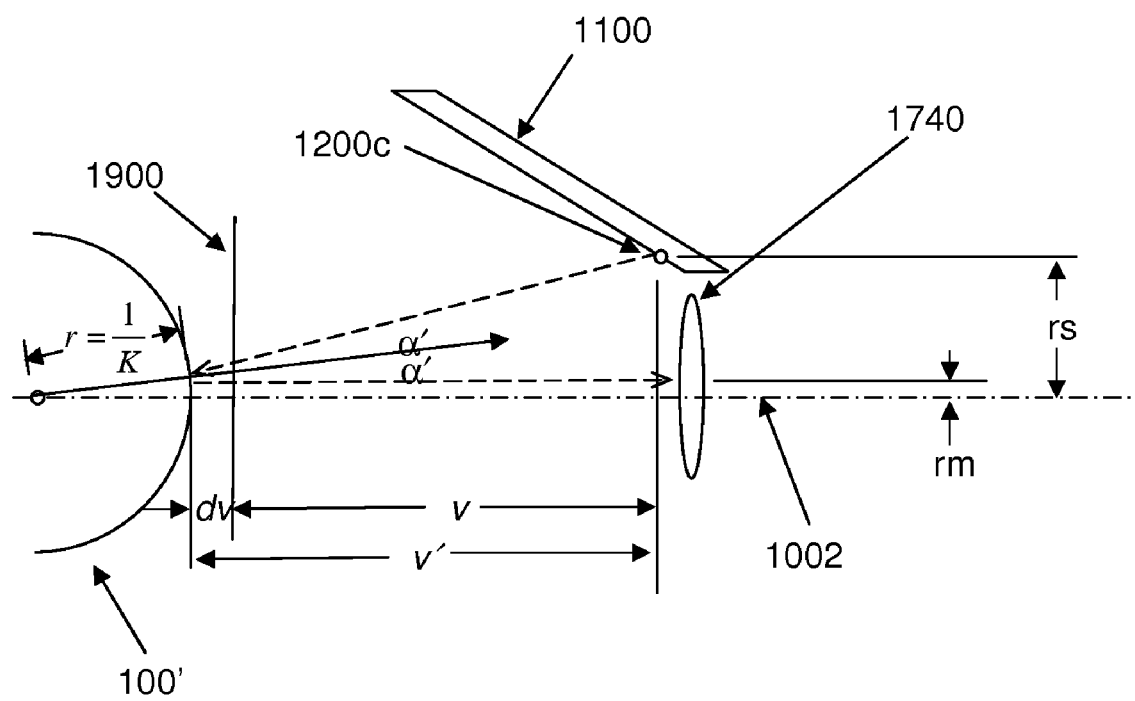
FIG. 13 illustrates a vertex error in a corneal topographer.

FIG. 13 illustrates a vertex error in a corneal topographer.

FIG. 13 illustrates the simple case of a spherical object or surface 100' with a radius of curvature illuminated by a Placido-type light source 1200c located at a radial distance from the optical axis of the corneal topographer, rs, and at an axial distance v from a reference plane or design corneal vertex plane 1900. The surface or object 100' may be that of an eye (real eye or model eye) or a test or calibration object. The vertex of surface or object 100' however does not necessarily touch the design corneal vertex plane 1900 but is generally located a distance dv from it. The distance dv is known as the vertex error and the axial distance from the source 1200c or system 1000 to the vertex of surface 100 is equal to v', where v' is equal to v+dv.

As may be seen in the figure, the ray from the source that reflects off the surface 100' so that following reflection it is parallel to the optical axis of the instrument makes an angle of 2α to the optical axis as it passes from the surface 100' to the reflection point. The radial distance of the reflection point from the optical axis is rm. This value is directly measured by the instrument.

The tangent of 2α' is given by the expression:

$$\tan(2\alpha') = \frac{(rs - rm)}{v'} \qquad (1)$$

The derivative of the tangent of 2α is then:

$$\frac{d\{\tan(2\alpha)\}}{dv'} = -\frac{(rs - rm)}{(v')^2} = -\frac{\tan(2\alpha)}{v'}$$

This allows the expression for the change in tangent of 2α' when distance v' changes by dv to be given as $$d\{\tan(2\alpha')\} = -\tan(2\alpha')\frac{dv'}{v'}$$

Using equation (1) this is:

$$d\{\tan(2\alpha')\} = -\left\{\frac{(rs-rm)}{v'}\right\}\frac{dv'}{v'} \quad (2)$$

FIG. 13 also illustrates that for a spherical surface 100' of curvature K, the relationship between the radial position of the reflection point, rm, the curvature, and the angle the surface 100' normal at the reflection point, α', is:

$$rm = r \cdot \sin\alpha' = \frac{\sin\alpha'}{K}, \text{ so that:} \quad (3)$$

$$K = \frac{\sin\alpha'}{rm}$$

The approximations are now made that:

$$\tan 2\alpha' = 2\alpha'$$

$$\sin \alpha' = \alpha'$$

These approximations are generally reasonable because reflection points close to the optical axis will be used in the vertex correction method to be given and for these points angle α is quite small. Then equations (1), (2) and (3) are approximated by:

$$2\alpha' = \frac{(rs-rm)}{v'} \quad (4)$$

$$d\{\tan(2\alpha')\} \cong -2\alpha'\frac{dv'}{v'}$$

$$K \cong \frac{\tan 2\alpha'}{2rm}$$

$$K \cong \frac{\alpha'}{rm} \quad (5)$$

The derivative of the curvature with respect to v' is then:

$$\frac{dK}{dv'} \cong \frac{1}{2rm}\frac{d(\tan 2\alpha')}{dv'}$$

So that the error is the curvature due to a vertex error, using equation (4), is:

$$dK \cong \frac{d(\tan 2\alpha')}{2rm} = -\frac{2\alpha'}{2rm}\frac{dv'}{v'} = -\left(\frac{\alpha'}{rm}\right)\frac{dv'}{v'}$$

Then using equation (5) this becomes:

$$dK \cong -K\frac{dv'}{v'} \quad (6)$$

It is informative to rearrange equation (6) to read:

$$\frac{dK}{K} \cong -\frac{dv'}{v'} \quad (7)$$

This shows that for the areas of interest in this method the percentage of curvature error equals the negative of the percentage of vertex error. For a vertex distance of 70 mm, for instance, a 1% vertex error equals 0.7 mm. For midrange corneal curvature values of 45 D, this then induces an error of 0.45 D. This amount of curvature difference is well within the resolution of the corneal topography system and so can be detected without difficulty. While this analysis is for the simple case of a spherical surface, the analysis for a toric surface is essentially the same, but for each meridional curvature. In the treatment below the surface 100' will be approximated by a surface that may be represented by a curvature matrix.

The inclusion of second light sources 1300 in system 1000 provides a means for calculating or estimating the vertex error for the Placido-type light source 1200c, thus allowing correction of or compensation for the curvature K based on an image of source 1200c on detector array 1400.

Second light sources 1300 have the remarkable characteristic that the light pattern generated from these sources can be analyzed to determine the base radius of the cornea independent of the distance to the cornea. The reason second light sources 1300 work differently than the light sources the conventional Placido-disk type corneal topographer is that the light from second light sources 1300 passes through the same optical element (e.g., lens 1740) twice instead of just once. Therefore, second light sources 1300 do not suffer from vertex errors.

Reference again to FIG. 1B may be used to help understand the insensitivity of the Helmholtz sources to distance from the cornea. Source 1300a is seen to provide a collimated beam 1301 that is directed toward cornea of eye 100 and may be thought to include bundle of parallel rays, three of which are the central ray and peripheral rays of beam 1301 represented by the solid line and dashed lines, respectively, in the figure. For the eye position shown in the figure, the central ray of beam 1301 is reflected off the cornea at point 1302, passes through aperture 1780, and is received by detector array 1400. If the eye 100 is moved axially from the position shown in the figure, a different, parallel ray from the beam 1301 is reflected off the cornea, but the new ray is also reflected at point 1302 and produces the same image on the detector array 1400. Thus, even if the eye is moved to a different axial location, the same data is produced by the detector array 1400.

For the central region of the cornea measured by second (central) light sources 1300, the points of reflection are directly measured and will be symbolized by xm(i,j) and ym(i,j). Here i and j are indices designating the source points. The surface normal components are known from the design of the instrument because all rays from the source that strike the surface have the same direction, so the angle they make with respect to the optical axis is the same for all. Due to the laws of reflection, this angle is twice that the surface normal makes to the optical axis and so this angle is also known by design. Knowledge of the angle the surface normal makes to the z axis of the coordinate system means that both of the gradient components are known. Thus for the system using the second (central) light sources 1300, the surface gradient components at the point of measurement, $$\frac{\partial S}{\partial x} \text{ and } \frac{\partial S}{\partial y}$$

are known by design and the reflection position is measured. If measurements are made for at least three rays in a surface neighborhood, then sufficient information is available to find a curvature matrix that characterizes the surface neighborhood. A curvature matrix [K] relates the local curvature, the measurement locations, and the gradients at those points via the following equation:

$$\begin{pmatrix} \frac{\partial S}{\partial x} \\ \frac{\partial S}{\partial y} \end{pmatrix} = \begin{bmatrix} Km+Kp & Kx \\ Kx & Km-Kp \end{bmatrix} \begin{pmatrix} xm \\ ym \end{pmatrix} \quad (8)$$

The elements of [K] are defined as: Km is the mean curvature of the local area; Kp is the curvature of a cross-cylinder like surface oriented with its principal axes aligned with the x and y axes; Kx is the curvature of a cross-cylinder like surface oriented with its principal axes aligned at 45 degrees to the x and y axes. The elements of [K] can be found in the following way.

For a surface whose central normal is aligned with the z axis:

$$[K] = \begin{bmatrix} Km+Kp & Kx \\ Kx & Km-Kp \end{bmatrix} = \quad (9)$$

$$\begin{vmatrix} \frac{\partial^2 S}{\partial x^2} & \frac{\partial^2 S}{\partial x \partial y} \\ \frac{\partial^2 S}{\partial x \partial y} & \frac{\partial^2 S}{\partial y^2} \end{vmatrix} = \begin{vmatrix} \frac{\partial}{\partial x}\left(\frac{\partial S}{\partial x}\right) & \frac{\partial}{\partial x}\left(\frac{\partial S}{\partial y}\right) \\ \frac{\partial}{\partial x}\left(\frac{\partial S}{\partial y}\right) & \frac{\partial}{\partial y}\left(\frac{\partial S}{\partial y}\right) \end{vmatrix}, \text{ so that}$$

$$Km+Kp = \frac{\partial\left(\frac{\partial S}{\partial x}\right)}{\partial x}, \quad Km-Kp = \frac{\partial\left(\frac{\partial S}{\partial y}\right)}{\partial y}, \quad Kx = \frac{\partial\left(\frac{\partial S}{\partial y}\right)}{\partial x} = \frac{\partial\left(\frac{\partial S}{\partial x}\right)}{\partial y}$$

If the measured points used to produce the three rays in the surface neighborhood are located in a quadrilateral as illustrated and labeled below:

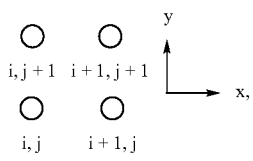

then the curvature matrix components can be expressed as finite difference approximations of equations (9) as:

$$Km+Kp = \frac{1}{2}\left\{ \frac{\left(\frac{\partial S}{\partial x}\right)_{i+1,j} - \left(\frac{\partial S}{\partial x}\right)_{i,j}}{xm_{i+1,j} - xm_{i,j}} + \frac{\left(\frac{\partial S}{\partial x}\right)_{i+1,j+1} - \left(\frac{\partial S}{\partial x}\right)_{i,j+1}}{xm_{i+1,j+1} - xm_{i,j+1}} \right\} \quad (10)$$

$$Km-Kp = \frac{1}{2}\left\{ \frac{\left(\frac{\partial S}{\partial y}\right)_{i,j+1} - \left(\frac{\partial S}{\partial y}\right)_{i,j}}{ym_{i,j+1} - ym_{i,j}} + \frac{\left(\frac{\partial S}{\partial y}\right)_{i+1,j+1} - \left(\frac{\partial S}{\partial y}\right)_{i+1,j}}{ym_{i+1,j+1} - ym_{i+1,j}} \right\}$$

$$Kx = \frac{1}{4}\left\{ \frac{\left(\frac{\partial S}{\partial x}\right)_{i,j+1} - \left(\frac{\partial S}{\partial x}\right)_{i,j}}{ym_{i,j+1} - ym_{i,j}} + \frac{\left(\frac{\partial S}{\partial x}\right)_{i+1,j+1} - \left(\frac{\partial S}{\partial x}\right)_{i+1,j}}{ym_{i+1,j+1} - ym_{i+1,j}} + \right.$$

$$\left. \frac{\left(\frac{\partial S}{\partial y}\right)_{i+1,j} - \left(\frac{\partial S}{\partial y}\right)_{i,j}}{xm_{i+1,j} - xm_{i,j}} + \frac{\left(\frac{\partial S}{\partial y}\right)_{i+1,j+1} - \left(\frac{\partial S}{\partial y}\right)_{i,j+1}}{xm_{i+1,j+1} - xm_{i,j+1}} \right\}$$

Here averaging of equivalent differences has been done to symmetrically use all data. The above derivation is illustrative only and is not the only way the curvature values can be found using the data from the second light sources. For example, the above method uses four data point to calculate the curvature matrix [K] and is especially effective when the data points form a generally rectangular pattern. In other embodiments, a curvature matrix [K] is calculated using only three data points or is calculated using an algorithm that accommodates irregularly spaced data point, for example, using an algorithm that uses a Hessian matrix.

If the central area is characterized by two principal curvature values, Kmax and Kmin and the axis value A for the principal meridian with the greater curvature value, the curvature matrix components are given by the equations:

$$Km = \frac{K\max + K\min}{2}$$

$$Kp = \frac{K\max - K\min}{2}\cos(2A)$$

$$Kx = \frac{K\max - K\min}{2}\sin(2A)$$

These curvature matrix values plus the measured reflection locations of the inner most Placido-type sources, xm and ym (where $rm^2 = xm^2 + ym^2$) and the known locations of the Placido-type sources, xs, ys and v (where $rs^2 = xs^2 + ys^2$), are used to find the vertex error dv in the following way.

Using the measured reflection locations, xm and ym, and the previously found values of Km, Kp and Kx, equation (8) is used to calculate the values of $$\frac{\partial S}{\partial x} \text{ and } \frac{\partial S}{\partial y}$$

for a given inner Placido-type source. The values of $$\frac{\partial S}{\partial x} \text{ and } \frac{\partial S}{\partial y}$$

are next used to calculate the components of the surface normal unit vector $$|N\rangle = \begin{pmatrix} Nx \\ Ny \\ Nz \end{pmatrix}$$

at the reflection point using the equations:

$$Nx = \frac{-\frac{\partial S}{\partial x}}{\sqrt{1+\left(\frac{\partial S}{\partial x}\right)^2+\left(\frac{\partial S}{\partial y}\right)^2}}$$

$$Ny = \frac{-\frac{\partial S}{\partial y}}{\sqrt{1+\left(\frac{\partial S}{\partial x}\right)^2+\left(\frac{\partial S}{\partial y}\right)^2}}$$

$$Nz = \frac{1}{\sqrt{1+\left(\frac{\partial S}{\partial x}\right)^2+\left(\frac{\partial S}{\partial y}\right)^2}}$$

Recognizing Nz as the cosine of the angle between the surface normal and the optical axis, $\alpha$, and that the plane of reflection passes through the optical axis and vector |N>, the angle of the ray striking the reflection point from the source and the optical axis is twice this angle so:

$$\tan(2\alpha) = \frac{\sin(2\alpha)}{\cos(2\alpha)} = \frac{2\sin(\alpha)\cos(\alpha)}{2\cos^2(\alpha)-1} = \frac{2\sqrt{1-\cos(\alpha)^2}\cos(\alpha)}{2\cos^2(\alpha)-1}$$

$$\tan(2\alpha) = \frac{Nz\sqrt{1-Nz^2}}{Nz-1/2}$$

But $\tan(2\alpha)$ is also equal to the radial distance between the reflection point and the source point divided by the axial distance between the reflection point and the source point. So:

$$\tan(2\alpha) = \frac{\sqrt{(xs-xm)^2+(ys-ym)^2}}{v'}$$

Solving for v' and using the expression for $\tan(2\alpha)$ as a function of Nz gives:

$$v' = \frac{\sqrt{(xs-xm)^2+(ys-ym)^2}}{\tan(2\alpha)} \quad (11)$$

$$= \frac{(Nz-1/2)\sqrt{(xs-xm)^2+(ys-ym)^2}}{Nz\sqrt{1-Nz^2}}$$

The axial distance between the reflection point and the source point, v', is the sum of the design vertex distance v, the surface sag at the reflection point, S(xm,ym), and the vertex error dv, so:

$$v'=v+S(xm,ym)+dv \text{ and}$$

$$v'-v-S(xm,ym)=dv \quad (12)$$

To find the value of S(xm,ym) the central portion of the surface is approximated by a surface given by the equation:

$$S(xm,ym) = \frac{Km(xm^2+ym^2)}{2} + \frac{Kp(xm^2-ym^2)}{2} + Kx(xm)(ym) \quad (13)$$

Equations (11), (12) and (13) are combined to give an equation for the vertex error:

$$dv = v - \frac{(Nz-1/2)\sqrt{(xs-xm)^2+(ys-ym)^2}}{Nz\sqrt{1-Nz^2}} - \frac{Km(xm^2+ym^2)}{2} - \frac{Kp(xm^2-ym^2)}{2} - Kx(xm)(ym) \quad (14)$$

This calculation may be done for each of the Placido-type sources located near the objective lens and the results averaged to given the best estimate of the vertex error. The averaged vertex error may give equal weight to each of the Placido-type sources used. Alternatively, the averaged vertex error may be a weighted average. For example, each vertex error based on a specific Placido-type source or set of Placido-type sources may be weighted, for example, based on a quality of the imaged source, a proximity to the outer edge of the central light source 1300 images, a local gradient value, or the like. The averaged vertex error may then be calculated based on the weighting of the individual data point from the Placido-type sources 1200.

Accordingly, the procedure described above may be summarized as: (1) determine the central radius of curvature in a central region of the cornea from data for the second (central) light sources 1300; (2) use the data near the outer edge of this ring of data—which is independent of the distance to the cornea—to analyze or compare with data for the innermost ring of the first light sources 1200. This radius of curvature data may be used to determine which curve the ray vs. z-distance falls upon. This plot can then be used to read out the z-distance (e.g., vertex distance, v' in FIG. 13) from the ray position. These steps can be performed iteratively, as necessary.

In certain embodiments, a system includes a range finder that comprises the light sources 1200 and 1300, the range finder being configured to determine a distance D between the system and the object or surface 100'. Data from the light sources 1200 and 1300 may be processed to determine a vertex error dv, for example, using the methodology disclosed above and/or Equation 14. For the system illustrated in FIG. 13, the system distance D between the object or surface 100' and system is:

$$D=v+dv$$

In this case, the system distance D is measured from the light source 1200c and is an axial distance (e.g., along a system optical axis); however, in general the system distance D may be measured from any feature, point, or plane of the system that is useful as a reference (e.g., a detector plane, the principal plane of a lens, or the like).

Using either the vertex error dv or the axial distance between the system and the vertex of the surface 100' (e.g., v or D), the entire surface of a test object may be reconstructed. It is obvious to those skilled in the art, that other analysis may likewise be employed to simultaneously determine the vertex error and use the entirety of spots from first and second light sources 1200 and 1300 to determine the corneal topography over the entire region measured. It will also be evident to those skilled in the art that range finding means, e.g., optical coherence tomography, may be employed to determine or eliminate the vertex error, and thus errors in the corneal topography for the data acquired with first light sources 1200.

Figure 14:
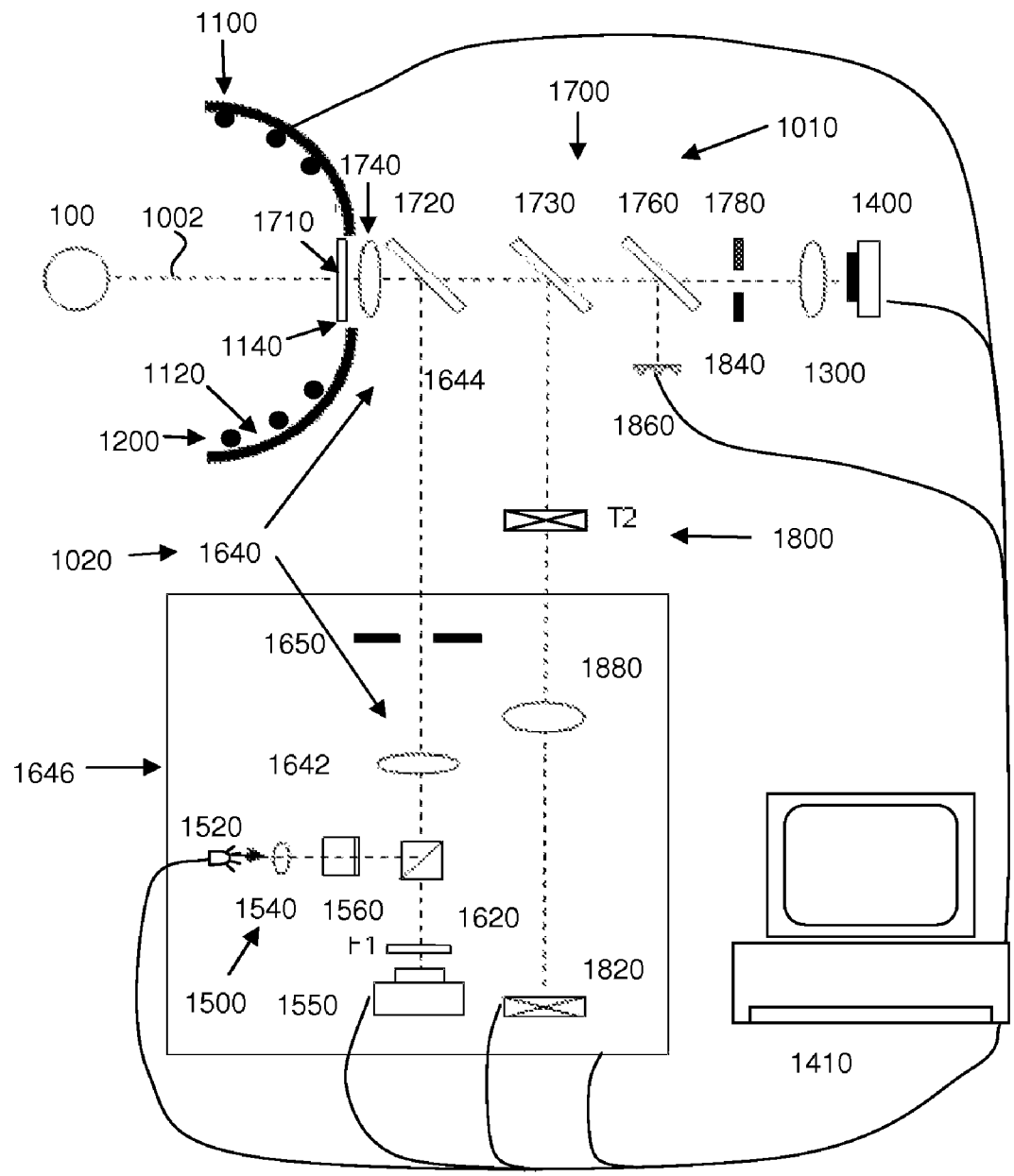
FIG. 14 shows another embodiment of a system for measuring aberrations and corneal topography of an eye.

FIG. 14 shows another embodiment of a system 2000 for measuring aberrations and corneal topography of an eye.

System 2000 is similar to system 1000 and so for brevity, only the differences between system 1000 and 2000 will be explained.

Compared to system 1000, in system 2000, the optical system 1700 is rearranged such that optical element (e.g., lens) 1740 is moved to be in the optical path between quarterwave plate 1710 and first beamsplitter 1720. An advantage of the arrangement of system 2000 is that it can potentially give better coverage of the central region of the cornea with first light sources 1200 than system 1000. A disadvantage of the arrangement of system 2000 is that optical element 1740 is now in the optical path of the wavefront measurement system, and can complicate the design of the adjustable telescope 1640 to allow the system to perform wavefront measurements over a desired measurement range.

Figure 15:
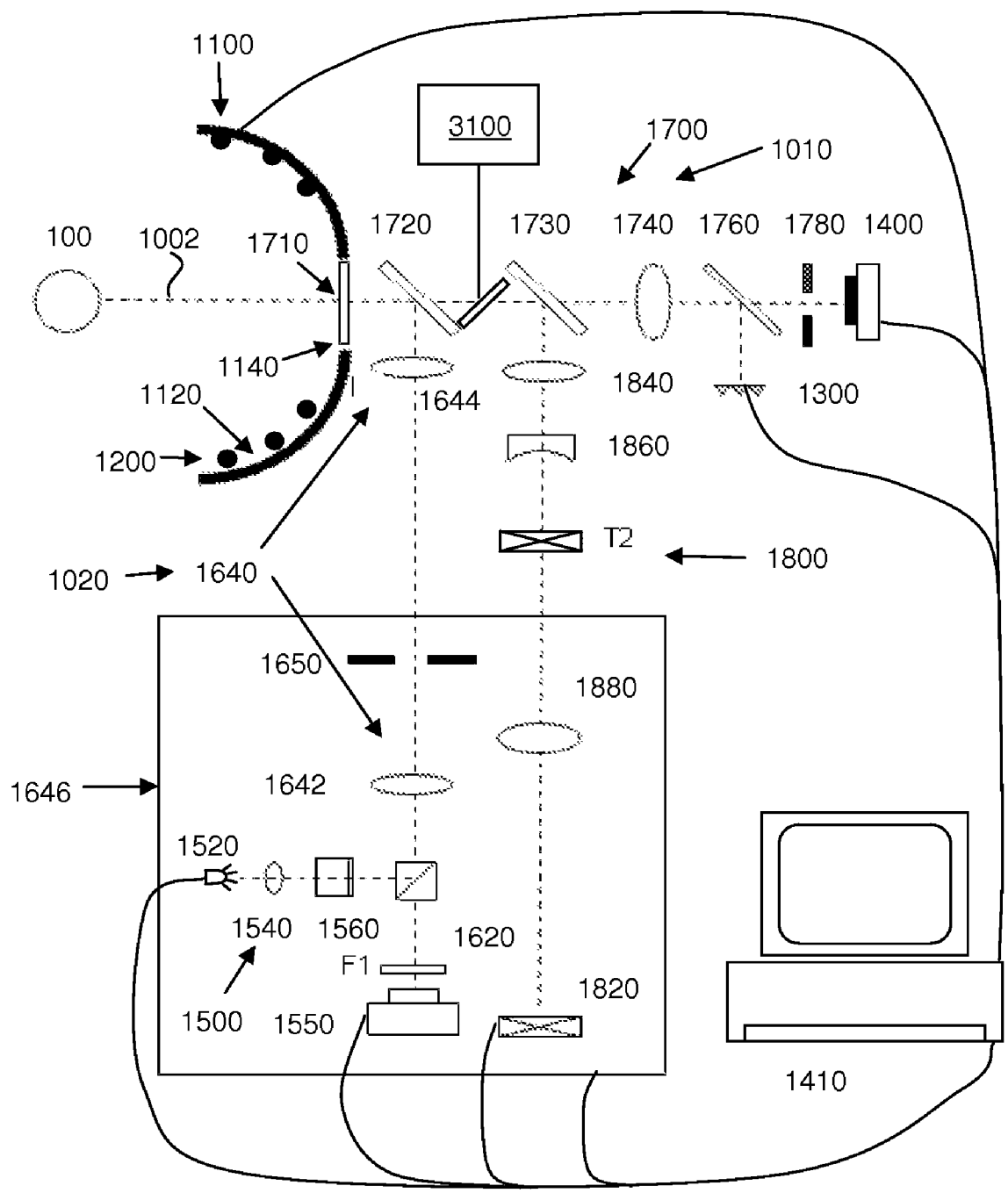
FIG. 15 shows another embodiment of a system for measuring the shape or location of an eye.
Figure 16:
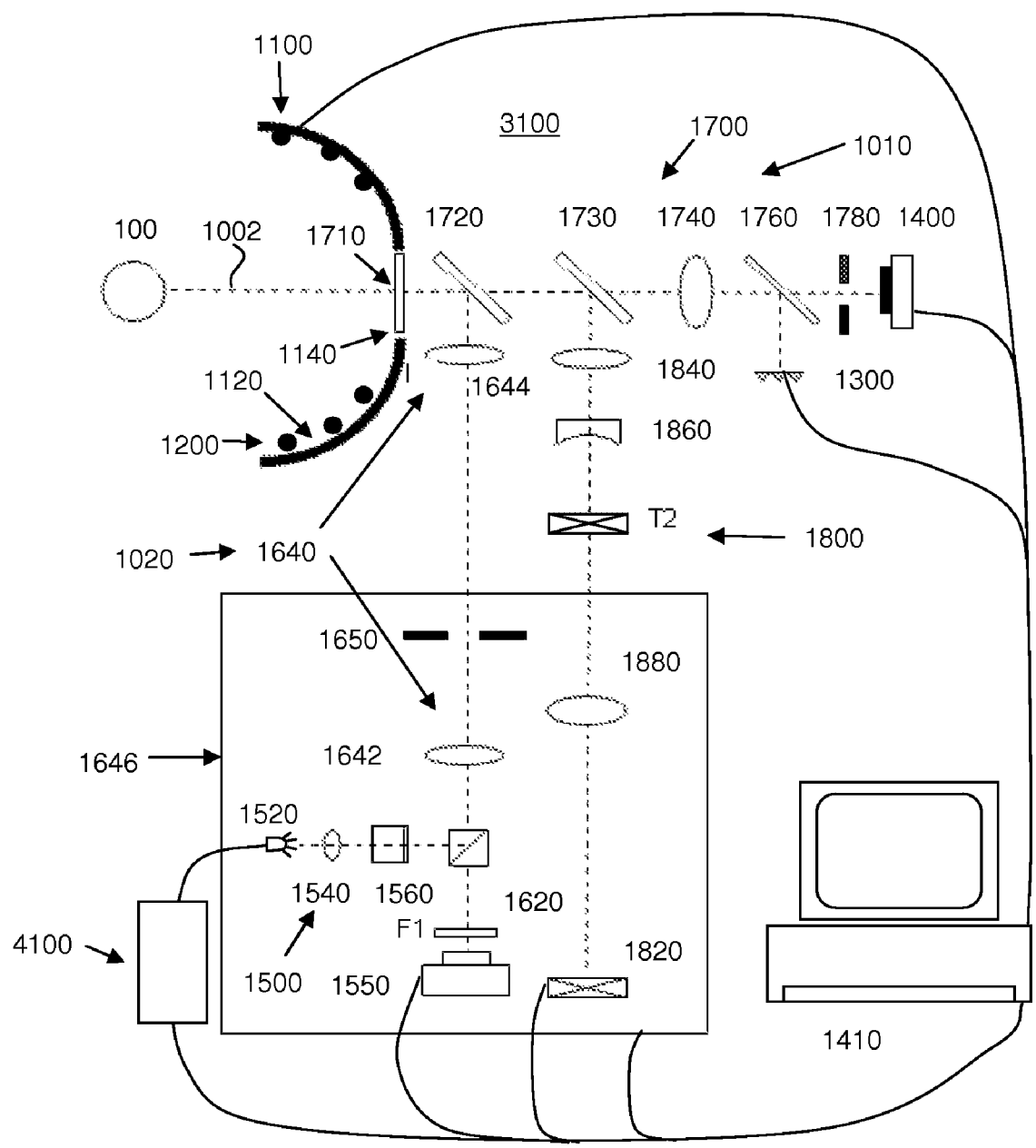
FIG. 16 shows another embodiment of a system for measuring the shape or location of an eye.

FIG. 15 shows an embodiment of the present invention comprising a system 3000 that is similar to the system 1000 shown in FIG. 1A. The system 3000 includes an OCT 3100 that is configured to provide biometry data. FIG. 16 shows an alternative system 4000 including an OCT 4100 that is coupled into the light source 1500. The OCTs 3100, 4100 advantageously provide direct and precise measurement of vertex error or system distance to the eye 100. Furthermore, the optical coherence tomographer can additionally provide valuable biometrical information, such as the corneal thickness, anterior chamber depth, crystalline lens thickness and lens to retinal distance, and the like. Such data, in combination with topography and aberrometry data provided by topographer 1010 and wavefront analyzer 1020, respectively, may be extremely useful in intraocular lens (IOL) implantation and corneal refractive procedures, such as LASIK or PRK surgery.

In certain embodiments, the systems 3000 or 4000 may be configured without the wavefront analyzer 1020 or without the topographer 1010. In other embodiments, the topographer 1010 and the OCTs 3100 or 4100 are used in combination to provide a vertex error of the eye 100 (or cornea) or a system distance between the vertex of the eye 100 (or cornea) and the system 1000 (e.g., the axial distance D derived above). For example, the OCT 3100 or 3200 is able to provide a very precise measure or estimate of the vertex error or system distance.

Figure 17:
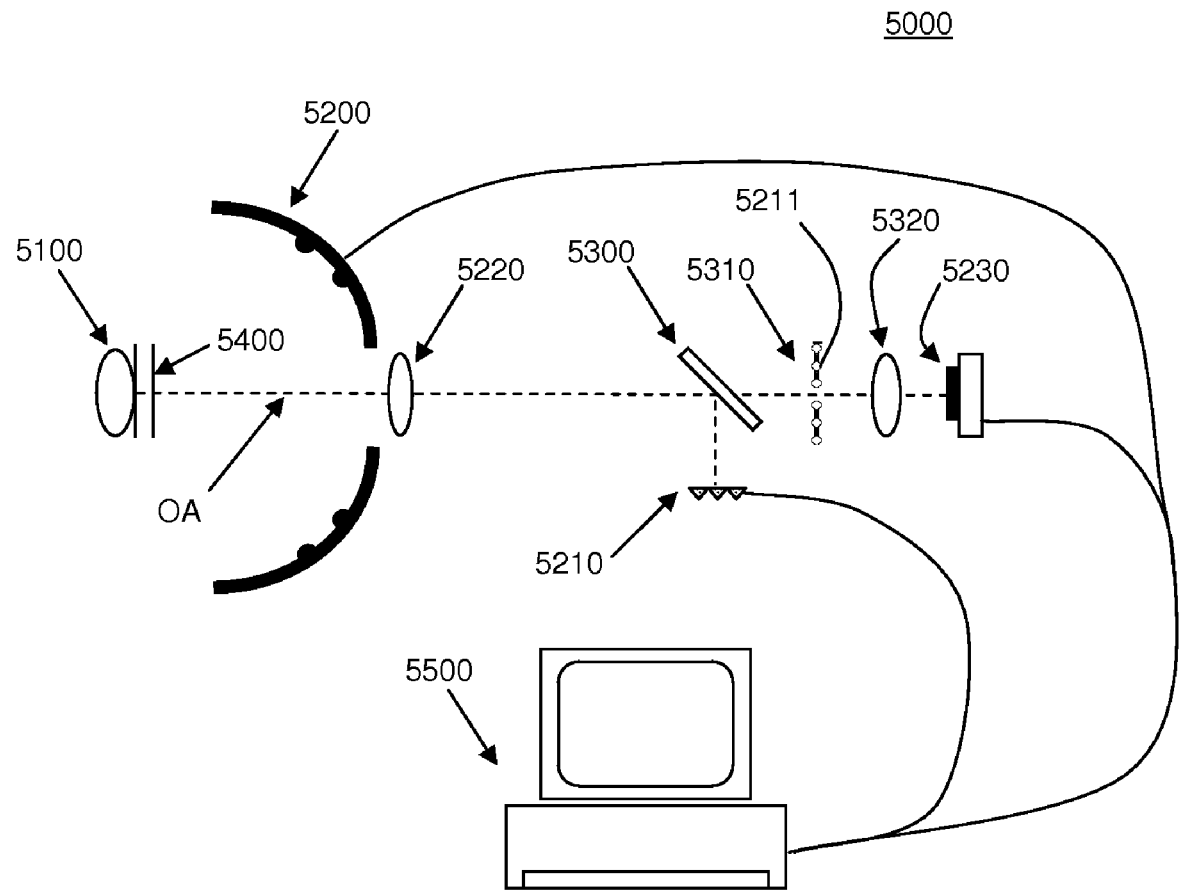
FIG. 17 shows an embodiment of a system for measuring the shape or location of an object to be measured or tested by the system.

FIG. 17 shows a system 5000 for measuring the shape and/or location of a test object 5100. The system 5000 may also used to measure or calculate other physical, geometric, or optical properties of the object 5100. The system 5000 may further include, or be integrated with, other optical components or measurement systems not shown in FIG. 17. Such measurement systems include, but are not limited to, an aberrometer, wavefront analyzer, interferometer, pupilometer, pachymeter, corneal microscope, biometer, tomographer, OCT, or the like. In certain embodiments, the system 5000 incorporates the use of polarization to measure the pachymetry. This may be accomplished by polarizing a cone spots, for example the light sources 1200 shown in FIGS. 1-7 or 12, then using a pair of cameras separated by a polarizing beam splitter to measure light from both polarizations.

The system 5000 is disposed along a central axis OA and is configured for measuring a vertex error of the test object 5100 and/or a distance of a test object 5100 from the system 5000. In certain embodiments, the system 5000 may also be used determine or calculate a shape of one or more surfaces of the test object 5100. The test object 5100 generally comprises at least one specularly reflective surface. In certain embodiments, the test object 5100 is an eye or cornea. In other embodiments, the test object 5100 is an optical element such as a mirror, lens, or an ophthalmic lens, such as a spectacle, a contact lens, an intraocular lens, a mold for a contact lens or intraocular lens, or the like. The system 5000 may include any of the elements, systems, methods, or functions previously discussed, where appropriate, of any of the systems 1000, 2000, 3000, 4000, or the system illustrated in FIG. 13. Additionally, any of the elements, systems, methods, or functions of the system 5000, where appropriate, may be incorporated into the systems 1000, 2000, 3000, 4000, or the system illustrated in FIG. 13.

The system 5000 includes a plurality of first light sources 5200, a plurality of second light sources 5210, a first optical element 5220, a detector, photodetector, or detector array 5230. In addition, the system 5000 may include a beamsplitter 5300, an aperture 5310, and a second lens 5320. The beamsplitter 5300 is useful for reflecting light from the plurality of second light sources 5210 to effectively locate the light sources 5210 along the central axis OA, preferably in a plane of the aperture 5310, for reasons similar to those discussed with regard to FIG. 1B. In such embodiments, the plurality of first light sources 5200 comprise individual light sources 5211 virtually located in the plane of the aperture 5310.

In the illustrated embodiment, the detector array 5230 is configured to receive light from the first and second light sources 5210, 5220 to form images thereof at or near the detector 5230 when the test object is located at or near a reference plane 5400. As discussed above, the distance between an apex of the test object 5100 and the reference plane 5400 may be referred to as a "vertex error". As also discussed above, a distance of the test object 5100 from the system 5000 may be considered to be the vertex error of the object 5100 plus the distance between a reference location of the system 5000 and the reference plane 5400. The reference location of the system 5000 may be any plane or point of the system that is considered appropriate. For example, the reference location may be the location of a relevant structural element of the system 5000, one of the individual light sources of the plurality of first light sources, the principal plane of an optical element such as the optical element 5220, a location of a focal length of an optical element such as a focal length of the optical element 5220, or the like. In certain embodiments, the reference location is the reference plane 5400 and the distance of the test object 5100 from the system 5000 is simply a vertex error.

The pluralities of first and second light sources 5200, 5210 may be a Placido-type light source and Helmholtz light source, respectively. As discussed above, at least some of the individual light sources of the plurality of second light sources 5210 may be used to evaluate or correct data produced by the plurality of first light sources 5200, since an image formed by the plurality of second light sources 5210 is independent or essentially independent of the location of the test object 5100 (the test object 5100 should generally be located such that sufficient light from the plurality of second light sources 5210 is reflected from the test object 5100 and back to the detector array 5230). In certain embodiments, the images of first light sources 5200 are near an outer periphery of images of the second light sources 5210, and the two sets of images may be evaluated and compared. In certain embodiments, a curvature of the test object 5100 is calculated using (1) the light sources of the outer periphery of second light sources 5210 and (2) the light sources of the inner portion of the first light sources 5200. If the curvatures calculated from each light source 5200, 5210 correspond to a same or comparable region of the test object 5100, then the curvature based on the first light sources 5200 may be corrected based on the curvatures calculated based on the second light sources

5210. Additionally or alternatively, calculations (e.g., of a curvature of the test object 5100) based on the plurality of second light sources 5210 may be compared to similar calculations made using the plurality of first light sources 5200 to calculate a vertex error and/or distances of the test object 5100 from the system 5000. In general, the accuracy a calculation of the curvature of the test object 5100, a calculation of a vertex error of the test object 5100, or a calculation of a distance of the test object 5100 from the system 5000 may be increased by incorporating a greater number of individual light sources 5200, 5210.

In certain embodiments—for example, if the light sources 5200, 5210 are used to calculate a vertex error or a distance of the test object 5100 from the system 5000, but not to calculate a curvature of the test object 5100—the light sources 5200, 5210 may each comprise only one, two, or a few individual light sources. Alternatively, the plurality of first light sources 5200 may comprise only light sources producing images at the detector array 5230 that are near corresponding images formed by the second plurality of light sources 5210, and visa versa. In either case, the number of light sources may be relatively few as compared to previous embodiments, since coverage of larger area of the test object 5100 in not needed, but only a comparison between light sources 5200 with corresponding light sources 5210.

In certain embodiments, the system 5000 includes an additional system (not shown) for determining the distances of the test object 5100 from the system 5000, for example, an optical system, such as an OCT light that shown in FIG. 15 or 16, which is able to provide a very precise distance measurement, but which may not be suitable alone for making such a measurement, as discussed above in relation to OCT measurements. Additionally or alternatively, the additional system may be used as a comparison to the distance measured using the light sources 5200, 5210, or may be in the alternative for situations where use of the light sources 5200 and/or 5210 are deemed inappropriate.

The system 5000 may also include a computer 5500 comprising a processor coupled to an electronic memory containing instructions and/or data used by the processor. The computer 5500 may be used to calculate or determine the location of light from the pluralities of first and second light sources 5200, 5210 on the detector array 5230, a vertex error of the test object 5100, a distance of the test object 5100 from the system 5000, and the like. The calculations may be made using the equations and methods discussed above as they relate to any of the systems 1000, 2000, 3000, or 4000, or the system illustrated in FIG. 13. The computer may be a commercially available desktop or laptop computer, or may be a specialized or customized electronic board or chip containing a processor and/or memory space.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A system for determining the shape of a surface of a test object, comprising:
   a first plurality of light sources disposed about a central axis, the light sources being separated from the central axis by radial distances defining an aperture in the first plurality;
   a second plurality of light sources;
   a detector array;
   an optical system adapted to provide light from the second plurality of light sources through the aperture to a test object; and
   an electronic memory comprising instructions to:
      calculate a first plurality of locations on the detector array of light from at least some of the first plurality of light sources when light from the first plurality of light sources is reflected off the test object;
      calculate a second plurality of locations on the detector array of light from at least some of the second plurality of light sources when light from the second plurality of light sources is reflected off the test object;
      determine a shape of a surface of the test object using the first plurality of locations and the second plurality of locations; and
   a processor to perform the instructions.

2. The system of claim 1, wherein the electronic memory further comprise instructions to adjust the first plurality of locations using the second plurality of locations.

3. The system of claim 1, wherein the electronic memory further comprises instructions to:
   calculate a distance of the test object from the system using the first plurality of locations and the second plurality of locations; and
   determine the shape of the surface of the test object using the distance.

4. The system of claim 1, wherein the electronic memory further comprises instructions to:
   calculate a first curvature of the surface using the first plurality of locations;
   calculate a second curvature of the surface using the second plurality of locations;
   determine the shape of the surface of the test object using the first and second curvatures.

5. The system of claim 1, wherein the electronic memory further comprises instructions to:
   calculate a first curvature of the surface using the first plurality of locations;
   calculate a second curvature of the surface using n the second plurality of locations;
   recalculate the first plurality of locations using the first curvature and the second curvature.

6. The system of claim 1, wherein the electronic memory further comprises instructions to:
   measure, using the second plurality of light sources, a curvature in an outer portion of a central region of the test object adjacent an outer region of the test object; and
   measure reflection locations from the test object of an innermost set of light sources of the first plurality of light sources; and
   calculate a distance of the test object from the system using (1) the measured curvature of the outer portion of the central region of the test object and (2) the measured reflection locations of the innermost set of light sources of the first plurality of light sources.

7. The system of claim 1, wherein the optical system comprises an optical element and, when the test object is disposed to reflect light from the first and second light sources, (1) light from the first plurality of light sources reflects off the test object, passes a first time through the optical element, and is received by the detector array, and (2) light from the second plurality of light sources passes a first time through the optical element, reflects off the test object, passes a second time through the optical element, and is received by the detector array.

8. The system of claim 7, wherein the optical element is a lens that is disposed to collimate light from the second plurality of light sources.

9. The system of claim 1, wherein the test object is a reference object having a know shape.

10. The system of claim 9, wherein the shape is a spherical shape with a constant radius of curvature.

11. The system of claim 1, wherein the test object is a spectacle lens, a contact lens, an intraocular lens, or a mold for forming a contact lens or intraocular lens.

12. The system of claim 1, wherein the test surface is a cornea of an eye.

13. The system of claim 1, wherein the first plurality of light sources forms a Placido-like light source and the second plurality of light sources forms a Helmholtz source.

14. A system for measuring a distance of a test object from the system, comprising:
a first light source and a second light source;
a detector array configured to receive light from the first and second light sources;
an electronic memory comprising instructions to:
measure one or more first locations on the detector array of light from the first light source;
measure one or more first locations on the detector array of light from the second light source; and
calculate the distance of the test object from the system using the measured first and second locations of light from the first and second light sources; and
a processor to perform the instructions;
wherein, when a test object is disposed to reflect light from the first and second light sources, (1) light from the first light source reflects off the test object, passes a first time through the optical element, and is received by the detector array, and (2) light from the second light source passes a first time through the optical element, reflects off the test object, passes a second time through the optical element, and is received by the detector array;
wherein the first light source, second light source, and the detector array are disposed for calculating the distance of the test object from the system.

15. The system of claim 14, wherein the optical element is a lens having a focal length configured to collimate light from the second light source.

16. The system of claim 14, wherein the distance of the test object from the system is a vertex error of the test object from a reference plane of the system.

17. The system of claim 14, wherein the distance of the test object from the system is a distance from a reference location of the system to the test object.

18. The system of claim 17, wherein the reference location is a location of the first light source.

19. The system of claim 17, wherein the reference location is a principal plane of the optical element or a distance one focal length of the optical element away from the optical element.

20. The system of claim 14, wherein the first light source comprises a first plurality of individual light sources and the second light source comprises a second plurality of individual light sources, the system further comprising an electronic memory comprising instructions to:
measure, using the second plurality of individual light sources, a curvature in an outer portion of a central region of the test object, adjacent an outer region of the test object; and
measure one or more reflection locations from the test object of an innermost set of individual light sources of the first plurality of individual light sources; and
calculate a distance of the test object from the system using (1) the measured curvature of the outer portion of the central region of the test object and (2) the measured reflection locations of the innermost set of individual light sources.

21. The system of claim 14, wherein the test object is a cornea of an eye.

22. The system of claim 14, wherein the test object is a spectacle lens, a contact lens, or an intraocular lens, or a mold for forming a contact lens or intraocular lens.

23. A method of determining a distance of a test object from the system, comprising:
providing a system including a first light source, a second light source, an optical element, and a detector array;
disposing a test object so that light from the first and second light sources is reflected off the test object;
passing light from the second light source a first time through the optical element, reflecting light off the test object, and passing the reflected light a second time through the optical element;
reflecting light from the first light source off the test object, passing the reflected light from the first light source a first time through the optical element;
receiving light from the first and second light sources at the detector array;
calculating a distance of the test object from the system using the received light from the first and second light sources at the detector array;
wherein the calculating comprises:
measuring one or more first locations on the detector array of light from the first light source;
measuring one or more first locations on the detector array of light from the second light source; and
calculating the distance of the test object from the system using the measured first and second locations of light from the first and second light sources.

24. A system for measuring a distance of a test object from the system, comprising:
a first light source and a second light source;
a detector array configured to receive light from the first and second light sources;
an electronic memory comprising instructions to:
measure one or more first locations on the detector array of light from the first light source;
measure one or more first locations on the detector array of light from the second light source; and
calculate the distance of the test object from the system using the measured first and second locations of light from the first and second light sources; and
a processor to perform the instructions;
wherein, when a surface of the test object is illuminated by light from the first and second light sources, (1) the first light source produces a signal at the detector array that depends on a shape of the surface of the test object and on a distance of the test object from the system, and (2) the second light source produces a signal at the detector array that depends on a shape of the surface of the test object and that does not depend on a distance of the test object from the system;
wherein the first light source, second light source, and the detector array are disposed for calculating the distance of the test object from the system.

25. The system of claim 24 wherein the first light source, second light source, and the detector array are disposed for calculating a shape of the surface of the test object.

* * * * *